United States Patent
Patel et al.

(10) Patent No.: US 10,196,612 B1
(45) Date of Patent: Feb. 5, 2019

(54) METHOD OF CHARACTERIZING AND MANIPULATING ADIPOSE STEM CELL DEPOTS TO A METABOLICALLY HEALTHY STATE

(71) Applicants: Niketa A. Patel, Land O' Lakes, FL (US); Ghattas El Bassit, Tampa, FL (US)

(72) Inventors: Niketa A. Patel, Land O' Lakes, FL (US); Ghattas El Bassit, Tampa, FL (US)

(73) Assignees: University of South Florida, Tampa, FL (US); The United States of America as Represented by the Department of Veterens Affairs, Washington, DC (US)

( * ) Notice: Subject to any disclaimer, the term of this patent is extended or adjusted under 35 U.S.C. 154(b) by 0 days.

(21) Appl. No.: 15/646,902

(22) Filed: Jul. 11, 2017

Related U.S. Application Data

(60) Provisional application No. 62/360,702, filed on Jul. 11, 2016.

(51) Int. Cl.
| | | |
|---|---|---|
| *C12N 5/0775* | (2010.01) | |
| *C07K 16/28* | (2006.01) | |
| *A61K 38/18* | (2006.01) | |
| *A61K 39/00* | (2006.01) | |

(52) U.S. Cl.
CPC ........ *C12N 5/0667* (2013.01); *A61K 38/1825* (2013.01); *C07K 16/2896* (2013.01); *A61K 2039/545* (2013.01); *C12N 2501/727* (2013.01); *C12N 2506/1384* (2013.01)

(58) Field of Classification Search
CPC ................ C12N 5/0667; C12N 2506/1384
See application file for complete search history.

(56) References Cited

U.S. PATENT DOCUMENTS

| | | | | |
|---|---|---|---|---|
| 2009/0304654 | A1* | 12/2009 | Lue ...................... | C12N 5/0667 424/93.21 |
| 2015/0004144 | A1 | 1/2015 | Cowan et al. | |
| 2015/0039917 | A1 | 2/2015 | Morikawa | |
| 2015/0202234 | A1 | 7/2015 | Gillette et al. | |
| 2015/0275177 | A1 | 10/2015 | West et al. | |
| 2017/0014455 | A1 | 1/2017 | Nie et al. | |

OTHER PUBLICATIONS

Prats et al., 1989, Proc.Nat.Acad. Sci. USA 86 (6): 1836-1840 (Year: 1989).*
Wang et al., Stem Cells 2010, 28:885-893 (Year: 2010).*
Carter, Gay, et al. Dysregulated Alternative Splicing Pattern of PKC during Differentiation of Human Preadipocytes Represents Distinct Differences between Lean and Obese Adipocytes. ISRN Obesity. 2013, 2013:9.
Carter, Gay, et al. Protein kinase C delta (PKCδ) splice variant modulates senescence via hTERT in adipose-derived stem cells. Stem Cell Investig 2014, 1:3.
Cawthorn, William P., et al. Adipose tissue stem cells meet preadipocyte commitment: going back to the future. Journal of lipid research. 2012;53(2):227-46. Epub Dec. 6, 2011.
Jiang, Kun, et al. Identification of a novel antiapoptotic human protein kinase C delta isoform, PKCδVIII in NT2 cells. Biochemistry 2008, 47:787-97.
Karastergiou, Kalpso, et al. Distinct developmental signatures of human abdominal and gluteal subcutaneous adipose tissue depots. J Clin Endocrinol Metab 2013, 98:362-71.
Patel, Rekha S., et al. Adipose-derived stem cells from lean and obese humans show depot specific differences in their stem cell markers, exosome contents and senescence: Role of Protein Kinase C delta (PKCδ) in adipose stem cell niche. Stem Cell Investigations. 2016, 3(1).
Patel, Rekha S., et al. Transformer 2β homolog (*Drosophila*) (TRA2B) regulates protein kinase C δI (PKCδI) splice variant expression during 3T3L1 preadipocyte cell cycle. J Biol Chem 2014, 289:31662-72.
Shi Jian-Guo, et al. Transdifferentiation of human adipose-derived stem cells into urothelial cells: potential for urinary tract tissue engineering. Cell and tissue research. 2012;347(3):737-46.
Watson, James E., et al. Comparison of Markers and Functional Attributes of Human Adipose-Derived Stem Cells and Dedifferentiated Adipocyte Cells from Subcutaneous Fat of an Obese Diabetic Donor. Adv Wound Care (New Rochelle) 2014, 3:219-228.
Yadav, Hariom, et al. Protection from obesity and diabetes by blockade of TGF-beta/Smad3 signaling. Cell metabolism. 2011, 14(1):67-79.
Onate, Bianca, et al. Stem cells isolated from adipose tissue of obese patients show changes in their transcriptomic profile that indicate loss in stemcellness and increased commitment to an adipocytelike phenotype. BMC Genomics 2013;14:625.

* cited by examiner

*Primary Examiner* — Daniel C Gamett
(74) *Attorney, Agent, or Firm* — Michele L. Lawson; Smith & Hopen, P.A.

(57) ABSTRACT

A method of reprogramming omental adipose cells to a subcutaneous-like lineage is presented herein. The method comprises exposing omental adipose cells to a small molecule such as Basic Fibroblast Growth Factor (bFGF); TRC105; long noncoding RNAs (lncRNAs) MALAT1, GAS5, linc-VLDLR; transcription factors Sox15, Oct4, KLF4, Nanog, Sal4, BMI1; or combinations thereof.

16 Claims, 12 Drawing Sheets

Specification includes a Sequence Listing.

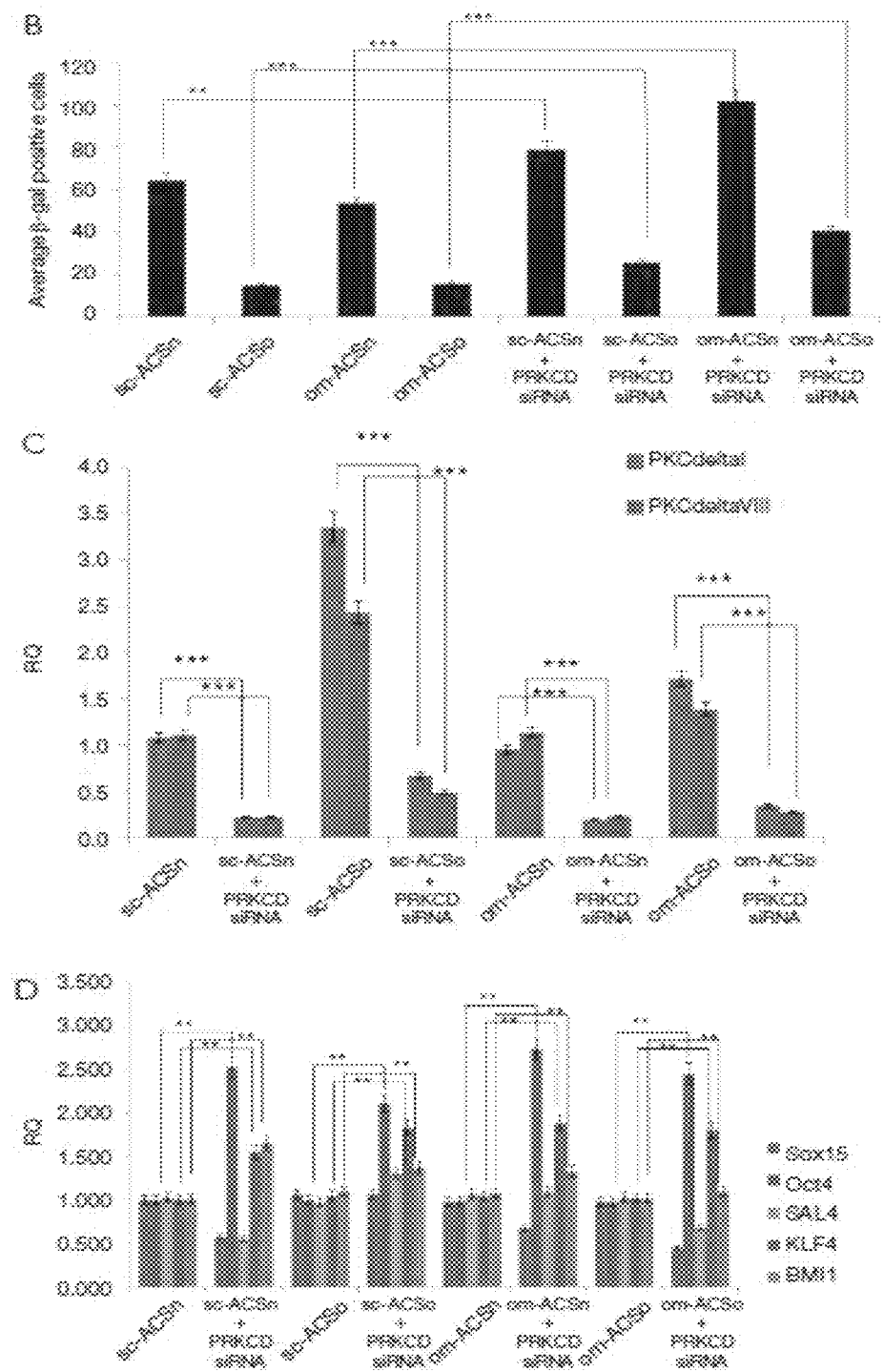
Figure 6B-D

Figure 7 continued

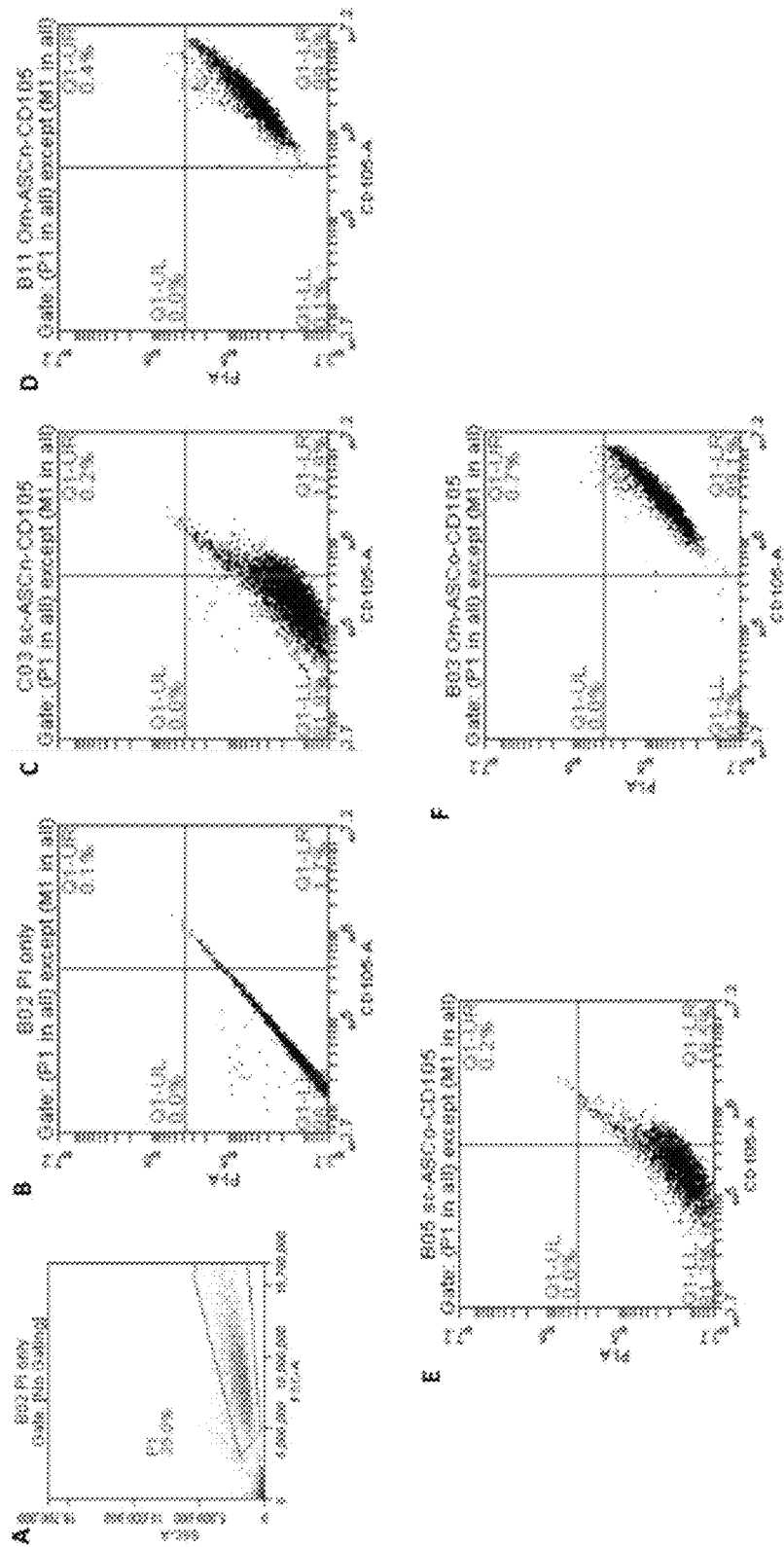
Figure 9A-F

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial sequence
<220> FEATURE:
<223> OTHER INFORMATION: Oct4 sense primer

<400> SEQUENCE: 1
tcccatgcat tcaaactgag g                                            21

<210> SEQ ID NO 2
<211> LENGTH: 20
<212> TYPE: DNA
<213> ORGANISM: artificial sequence
<220> FEATURE:
<223> OTHER INFORMATION: Oct4 antisense primer

<400> SEQUENCE: 2
ccaaaaccct ggcacaaact                                              20

<210> SEQ ID NO 3
<211> LENGTH: 21
<212> TYPE: DNA
<213> ORGANISM: artificial sequence
<220> FEATURE:
<223> OTHER INFORMATION: Sal4 sense primer

<400> SEQUENCE: 3
gcccagatat cctggaaacc a                                            21

<210> SEQ ID NO 4
<211> LENGTH: 22
<212> TYPE: DNA
<213> ORGANISM: artificial sequence
<220> FEATURE:
<223> OTHER INFORMATION: Sal4 antisense primer

<400> SEQUENCE: 4
ttctcggagc tctcttgctt tg                                           22

<210> SEQ ID NO 5
<211> LENGTH: 21
<212> TYPE: DNA
<213> ORGANISM: artificial sequence
```

```
<220> FEATURE:
<223> OTHER INFORMATION: Sox15 sense primer

<400> SEQUENCE: 5
gaacaggttg gaagcaaagg c                                              21

<210> SEQ ID NO 6
<211> LENGTH: 21
<212> TYPE: DNA
<213> ORGANISM: artificial sequence
<220> FEATURE:
<223> OTHER INFORMATION: Sox15 antisense primer

<400> SEQUENCE: 6
gaacaggttg gaagcaaagg c                                              21

<210> SEQ ID NO 7
<211> LENGTH: 20
<212> TYPE: DNA
<213> ORGANISM: artificial sequence
<220> FEATURE:
<223> OTHER INFORMATION: KLF4 sense primer

<400> SEQUENCE: 7
ctgcggcaaa acctacacaa                                                20

<210> SEQ ID NO 8
<211> LENGTH: 19
<212> TYPE: DNA
<213> ORGANISM: artificial sequence
<220> FEATURE:
<223> OTHER INFORMATION: KLF4 antisense primer

<400> SEQUENCE: 8
ggtcgcattt ttggcactg                                                 19

<210> SEQ ID NO 9
<211> LENGTH: 19
<212> TYPE: DNA
<213> ORGANISM: artificial sequence
<220> FEATURE:
<223> OTHER INFORMATION: BMI1 sense primer

<400> SEQUENCE: 9
aatgtctttt ccgcccgct                                                 19

<210> SEQ ID NO 10
<211> LENGTH: 23
<212> TYPE: DNA
<213> ORGANISM: artificial sequence
<220> FEATURE:
<223> OTHER INFORMATION: BMI1 antisense primer

<400> SEQUENCE: 10
accctccaca aagcacacca cat                                            23

<210> SEQ ID NO 11
<211> LENGTH: 20
<212> TYPE: DNA
<213> ORGANISM: artificial sequence
<220> FEATURE:
<223> OTHER INFORMATION: PKCdeltaVIII sense primer

<400> SEQUENCE: 11
tgggtccatt gccccattac                                                20
```

```
<210> SEQ ID NO 12
<211> LENGTH: 20
<212> TYPE: DNA
<213> ORGANISM: artificial sequence
<220> FEATURE:
<223> OTHER INFORMATION: PKCdeltaVIII antisense primer

<400> SEQUENCE: 12
cgtaggtccc actgttgtcc                                              20

<210> SEQ ID NO 13
<211> LENGTH: 24
<212> TYPE: DNA
<213> ORGANISM: artificial sequence
<220> FEATURE:
<223> OTHER INFORMATION: PKCdeltaI sense primer

<400> SEQUENCE: 13
acatcctagg tacaacaacg ggac                                         24

<210> SEQ ID NO 14
<211> LENGTH: 21
<212> TYPE: DNA
<213> ORGANISM: artificial sequence
<220> FEATURE:
<223> OTHER INFORMATION: PKCdeltaI antisense primer

<400> SEQUENCE: 14
accacgtcct tcttcagaca c                                            21
```

METHOD OF CHARACTERIZING AND MANIPULATING ADIPOSE STEM CELL DEPOTS TO A METABOLICALLY HEALTHY STATE

CROSS REFERENCE TO RELATED APPLICATIONS

This application is a nonprovisional of and claims priority to U.S. Provisional Patent Application No. 62/360,702, entitled "Method of Characterizing and Manipulating Adipose Stem Cell Depots to a Metabolically Healthy State", filed Jul. 11, 2016, the entire contents of which is herein incorporated into this disclosure.

FIELD OF INVENTION

This invention relates to obesity. Specifically, the invention describes methods of reprogramming omental adipose stem cells to a subcutaneous-like lineage to treat obesity.

BACKGROUND OF THE INVENTION

Obesity is one of the most prevalent health conditions with about 30% of the world's adult population being either overweight or obese, causing an increased risk for cardiovascular diseases, diabetes, and certain types of cancer. (Ng, M., Fleming, T., Robinson, M., Thomson, B., Graetz, N., Margono, C., Mullany, E. C., Biryukov, S., Abbafati, C., Abera, S. F., et al.: Global, regional, and national prevalence of overweight and obesity in children and adults during 1980-2013: a systematic analysis for the global burden of disease study 2013. The Lancet 384(9945), 766-781 (2014)) Central obesity, also known as abdominal obesity, is the excessive build-up of fat around stomach and abdomen. Central obesity has been held responsible for high levels of LDL cholesterol and triglycerides and lower levels of HDL cholesterol.

Obesity contributes to increased heart disease, diabetes, and the likelihood of over 65 other diseases. (Wang, A, Kinsinger, L S, Kahwati, L C, Das, S R, Gizlice, Z, Harvey, R T, Burdick, M B & Yevich, S J. Obesity and weight control practices in 2000 among veterans using V A facilities. *Obes Res* 13, (2005)).

Human adult stem cells can regenerate the cellular population via self-renewal and their ability to differentiate and maintain asymmetric cellular division. The hematopoietic and mesenchymal stem cells were predominantly characterized and studied for stem cell markers and differentiation into specific lineages. Since then, it is now recognized that stem cells reside within stem cell niches of the adult organ where the number of stem cells are regulated. Amongst these, the adipose-derived stem cells (ASCs) show great therapeutic potential in regenerative medicine as they are relatively easy to isolate and are obtained at higher yields.

Human ASCs reside within the stromal vascular fraction (SVF) of the adipose tissue. ASC maintain a quiescent stage in vivo and can undergo differentiation into adipocytes, osteoblasts or chondrocytes (Carter G, Apostolatos A, Patel R, et al. Dysregulated Alternative Splicing Pattern of PKCδ during Differentiation of Human Preadipocytes Represents Distinct Differences between Lean and Obese Adipocytes. ISRN Obes 2013, 2013:161345; Watson J E, Patel N A, Carter G, et al. Comparison of Markers and Functional Attributes of Human Adipose-Derived Stem Cells and Dedifferentiated Adipocyte Cells from Subcutaneous Fat of an Obese Diabetic Donor. Adv Wound Care (New Rochelle) 2014, 3:219-228). ASC maintain their self-renewal ability by expressing transcriptional factors that regulate its ability to differentiate. Tissue damage and diseases often cause the ASC to undergo hyperproliferation leading to dysfunctional cells. It was previously shown that the ASC obtained from obese patients have distinct differences in their genetic profiles during differentiation to adipocytes compared to lean (Carter 2013). In addition, it is known that depot-specific differences are prominent in white adipose tissue. For example, leptin is produced predominantly by subcutaneous adipose tissue; adiponectin is expressed higher in omental adipose tissue.

Excess omental fat is central to increased risk factor for cardiovascular diseases and diabetes mellitus. Protein kinase C is a family of serine/threonine kinases with 11 isoforms. The primary amino acid structure of PKCs can be divided into conserved regions (C1-C4) separated by the variable regions (V1-V5). All PKCs have an N-terminal regulatory domain and a C-terminal catalytic domain separated by the V3 hinge region. The protein kinase C family is subdivided into three groups based upon their activation by calcium, phosphatidyl serine, diacyl glycerol or phorbol esters: classical or conventional PKCs ($\alpha$, $\beta$I, $\beta$II and $\gamma$), novel PKCs ($\delta$, $\epsilon$, $\eta$ and $\theta$) and atypical PKCs ($\zeta$, $\lambda/\iota$). PKCs are also activated by proteolytic cleavage at the V3 hinge region by calpain I, II or caspase-3 to generate a constitutively active catalytic domain of PKC.

PKCδ, a novel PKC, plays an important role in cellular differentiation, proliferation and apoptosis. In addition, several reports have indicated the role of PKCδ in stem cell differentiation (Hamdorf M, Berger A, Schüle S, et al. PKCδ-induced PU.1 phosphorylation promotes hematopoietic stem cell differentiation to dendritic cells. Stem Cells 2011, 29:297-306; Lee H J, Jeong C H, Cha J H, et al. PKC-delta inhibitors sustain self-renewal of mouse embryonic stem cells under hypoxia in vitro. Exp Mol Med 2010, 42:294-301). PKCδ is alternatively spliced to generate PKCδI and PKCδVIII variants in humans (Patel N A, Song S S, Cooper D R. PKCdelta alternatively spliced isoforms modulate cellular apoptosis in retinoic acid-induced differentiation of human NT2 cells and mouse embryonic stem cells. Gene Expr 2006, 13:73-84; Jiang K, Apostolatos A H, Ghansah T, et al. Identification of a novel antiapoptotic human protein kinase C delta isoform, PKCδVIII in NT2 cells. Biochemistry 2008, 47:787-97). The inventors have previously shown the expression of PKCδ splice variants in the ASC as well as the role of PKCδVIII in regulating hTERT in senescence (Carter G, Patel R, Apostolatos A, et al. Protein kinase C delta (PKCδ) splice variant modulates senescence via hTERT in adipose-derived stem cells. Stem Cell Investig 2014, 1:3).

The inventors have investigated the differences in stem cells derived from subcutaneous and omental adipose depots from a lean and an obese donor. Stem cell markers, exosomes and cellular senescence in the ASC isolated from different depots were compared and the role of PKCδ in ASC niche was evaluated.

SUMMARY OF INVENTION

The inventors characterized the ASC derived from subcutaneous and omental depots from a lean donor (sc-ASCn and om-ASCn) and compared it to the ASC derived from an obese donor (sc-ASCo and om-ASCo) using flow cytometry and real time qPCR. The inventors have shown that stem cell markers Oct4, Sal4, Sox15, KLF4 and BMI1 have distinct expression patterns in each ASC. The inventors evaluated the secretome of the ASC and characterized their secreted exosomes. Long noncoding RNAs (lncRNAs) were shown to be secreted by ASC and their expression varied between the ASC's derived from different depots.

Protein kinase C delta (PKCδ) regulates the mitogenic signals in stem cells. The inventors evaluated the effect of silencing PKCδ in sc-ASCn, om-ASCn, sc-ASCo and om-ASCo. Using β-galactisodase staining, the percentage of senescent cells in sc-ASCn, om-ASCn, sc-ASCo and om-ASCo was evaluated. The results also indicated that silencing PKCδ increases the percentage of senescent cells. The inventors demonstrate a role of PKCδ in maintaining the adipose stem cell niche and importantly demonstrate depot-specific differences in adipose stem cells and their exosome content.

This knowledge was used to reprogram obese omental adipose stem cells to subcutaneous-like lineage. Visceral/omental fat is correlated to glucose intolerance, insulin resistance, hepatosteatosis, as well as in ectopic fat distribution in cardiac, skeletal and hepatic tissue significantly contributing to metabolic dysfunction. In contrast, subcutaneous fat often serves as a protective depot against the comorbidities of obesity. The inventors identified factors that modulate the omental adipose stem cells such that it differentiates into a subcutaneous-like phenotype in order to reduce obesity comorbidities not by reducing fat content but by changing its metabolic profile. The inventors have also designed and engineered a novel adipose stem cell line which is a hybrid of omental and subcutaneous depots.

In an embodiment, a method of altering omental adipose cells metabolic profile to a subcutaneous adipose cells metabolic profile is presented comprising exposing the omental adipose cells to a therapeutically effective amount of a small molecule selected from the group consisting of long noncoding RNAs (lncRNAs), endoglin inhibitors, growth factors and combinations thereof. The growth factor can be Basic Fibroblast Growth Factor (bFGF) at a dosage of between about 100-500 nm. The endoglin inhibitor can be TRC105 at a dosage of between about 5-50 nm. TRC105 can be used in combination with bFGF in some embodiments. The lncRNAs can be MALAT1, GAS5, linc-VLDLR, and combinations thereof.

In another embodiment, a method of reducing obesity comorbidities in a patient is presented comprising administering a therapeutically effective amount of a small molecule to the patient to differentiate omental adipose cells into a subcutaneous-like phenotype wherein the small molecule is selected from the group consisting of Basic Fibroblast Growth Factor (bFGF), TRC105, long noncoding RNAs (lncRNAs) MALAT1, GAS5, linc-VLDLR, or combinations thereof. Basic Fibroblast Growth Factor (bFGF) can be administered at a dosage of between about 100-500 nm. TRC105 can be administered at a dosage of between about 5-50 nm. TRC105 can be used in combination with bFGF in some embodiments.

In a further embodiment, a method of treating obesity in a patient in need thereof is presented comprising differentiating omental adipose cells into a subcutaneous-like phenotype by administrating a small molecule selected from the group consisting of Basic Fibroblast Growth Factor (bFGF), TRC105, long noncoding RNAs (lncRNAs) MALAT1, GAS5, linc-VLDLR, or combinations thereof. Basic Fibroblast Growth Factor (bFGF) can be administered at a dosage of between about 100-500 nm. TRC105 can be administered at a dosage of between about 5-50 nm. TRC105 can be used in combination with bFGF in some embodiments.

BRIEF DESCRIPTION OF THE DRAWINGS

For a fuller understanding of the invention, reference should be made to the following detailed description, taken in connection with the accompanying drawings, in which:

FIG. 6A-D is a series of images depicting Senescence in ASC. (A) sc-ASCn, om-ASCn, sc-ASCo and om-ASCo were transfected with 50 nM PRKCD siRNA for 48 h. Cells were stained for β-galactosidase to detect senescence. Cells were then visualized under 4× light microscopy using Nikon Eclipse microscope. The percent of cells staining positive was calculated by counting five areas of the same size from each field per sample using NIS elements advance research image tool software. (B) The graphs show average of β-gal positive cells. Statistical analysis performed by two-tail Student's t-test. (C) Total RNA was isolated and real time qPCR was performed using PKCδI and PKCδVIII primers. The graph shows relative quotient (RQ). Statistical analysis performed by two-tail Student's t-test. (D) Total RNA was isolated and real time qPCR was performed using transcription factor Oct4, Sal4, Sox15, KLF4 and BMI1 primers. The graph shows relative quotient (RQ). Statistical analysis performed by two-tail Student's t-test. , P<0.01; *, P<0.001.

FIG. 9A-F is a series of images depicting representative scatter patterns for ASC cell populations stained with CD105. Percentage of CD 105 positive cells is indicated in the lower right quadrant (as determined by Accuri C6 instrument software). Absence of a fluorescent signal was interpreted as negative expression for that particular stem cell marker. Panel A—Indicates gating of cell population for analysis. Panel B—unstained control. Panel C—sc-ASCn CD105 stained. Panel D—Om-ASCn CD105 stained. Panel E—sc-ASC0-CD105 stained. Panel F Om-ASCo-CD 105 stained.

DETAILED DESCRIPTION OF THE PREFERRED EMBODIMENT

Figure 1:
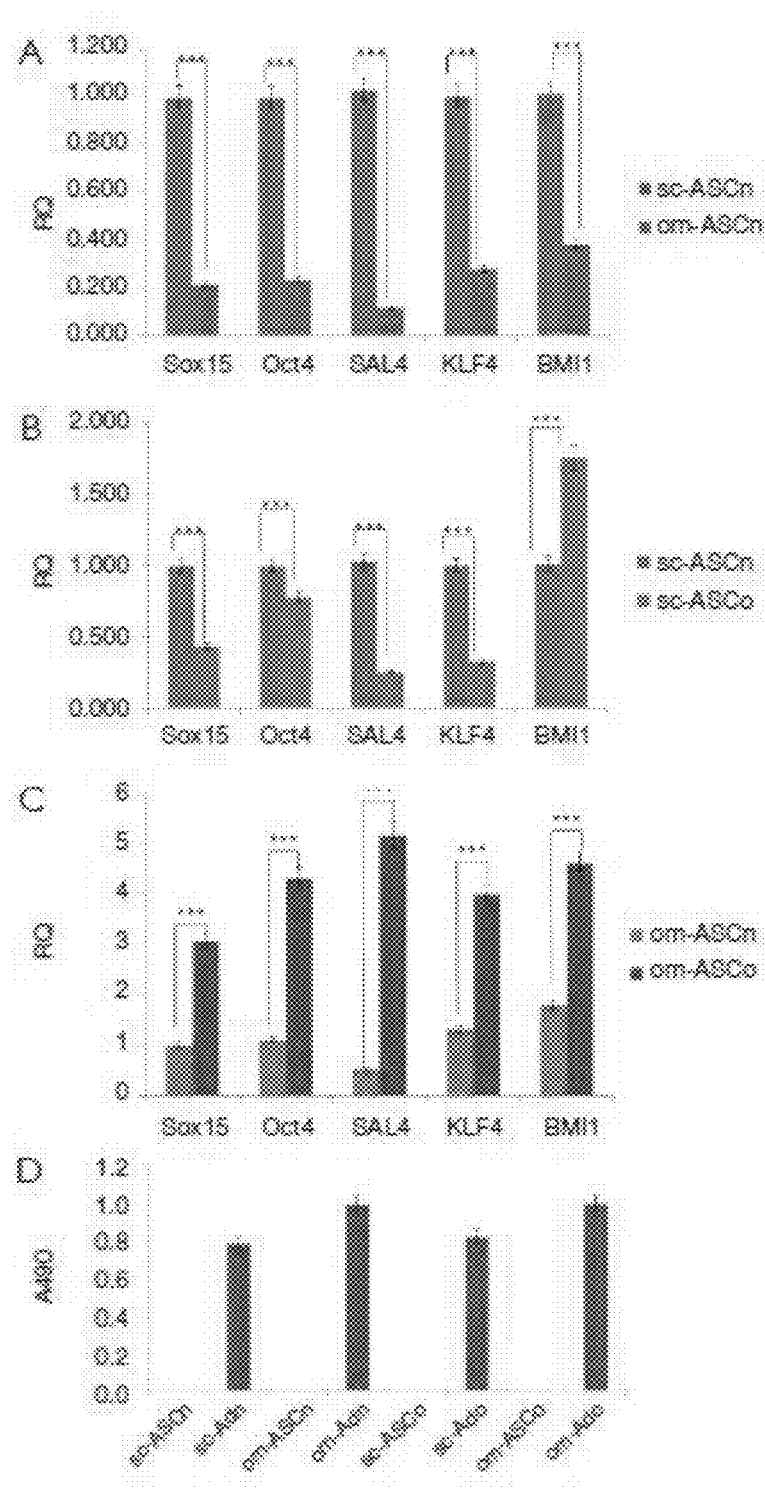
FIG. 1A-D are a series of images depicting Comparison of stem cell transcription factors. Expression of stem cell transcription factors in sc-ASCn, om-ASCn, sc-ASCo and om-ASCo were determined by real time qPCR. Total RNA was collected and real time qPCR was used to measure expression of Sox15, Oct4, SAL4, KLF4, BMI1. (A-C) shows relative quantification (RQ). The experiment was independently repeated 5 times with similar results. Statistical analysis performed by 2-way analysis of variance. (D) sc-ASCn, om-ASCn, sc-ASCo and om-ASCo were differentiated in vitro to mature adipocytes. The lipid droplets were stained with Oil Red O. The dye was extracted using isopropanol and absorbance was read at 490 nM. The ASCs do not have lipid accumulation while the mature adipocytes (Ad) derived from the respective ASCs show lipid staining. The experiments were independently repeated five times with similar results. ***, $P<0.001$.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise.

"Subject" is used to describe an animal, preferably a human, on whom the present system and method are used. "Subject" and "patient" are used interchangeably herein.

The term "about" as used herein is not intended to limit the scope of the invention but instead encompass the specified material, parameter or step as well as those that do not materially affect the basic and novel characteristics of the invention. In some instances, the term "about" refers to ±10%.

The term "cell" or "cells" is used synonymously herein and refers to in vitro cultures of mammalian cells grown and maintained as known in the art, as well as biological samples obtained from tumor specimens or normal specimens in vivo.

"White adipose tissue (WAT)" as used herein refers to a type of fat tissue in mammals which is used mainly for the storage of triglycerides during energy consumption and fatty acid release during energy expenditure. WAT can be used as a source of energy, for heat insulation and as a mechanical cushion.

"Visceral adipose tissue (VAT)" as used herein refers to white adipose tissue which is located around inner organs in mammals. VAT in the abdomen can further divided into omental and mesenteric with mesenteric being more deeply buried such as surrounding the intestine.

"Subcutaneous adipose tissue (SAT)" as used herein refers to white adipose tissue which is located beneath the skin in mammals. SAT is less metabolically active than VAT.

"Adipose-derived stem cells" or "ASC" as used herein refers to stem cells that have been derived from adipose tissue, particularly those derived from white adipose tissue.

"Omental depots" as used herein refers to the storage of omental adipose tissue around the inner organs in mammals.

Omental adipose tissue is a subset of visceral adipose tissue which is a type of white adipose tissue.

"Subcutaneous depots" as used herein refers to the storage of subcutaneous adipose tissue beneath the skin in mammals. Subcutaneous adipose tissue is a type of white adipose tissue.

"Scutal" as used herein refers to a hybrid stem cell that is formed from om-ASCo and sc-ASCn stem cells that are sorted by FACS and seeded into fresh plates to bring om-ASCo stem cell transcription factor expression levels to sc-ASCn stem cell transcription factor expression levels.

"Subcutaneous lean ASC (sc-ASCn)" as used herein refers to adipose-derived stem cells obtained from the subcutaneous depot of a lean mammal.

"Subcutaneous obese ASC (sc-ASCo)" as used herein refers to adipose-derived stem cells obtained from the subcutaneous depot of an obese mammal.

"Omental obese ASC (om-ASCo)" as used herein refers to adipose-derived stem cells obtained from the omental depot of an obese mammal.

"Omental lean ASC (om-ASCn)" as used herein refers to adipose-derived stem cells obtained from the omental depot of a lean mammal.

"Body mass index (BMI)" as used herein refers to a measure of obesity and metabolic health in humans in which the body mass (weight) divided by the square of the body height and is expressed in units of $kg/m^2$. Generally accepted ranges include: under 18.5 $kg/m^2$=underweight; 18.5 to 25 kg/m=normal; 25 to 30 $kg/m^2$=overweight; and over 30 $kg/m^2$=obese.

"Lean" as used herein refers to a human, having a body mass index (BMI) below 25.

"Obese" as used herein refers to a human, having a body mass index (BMI) above 30.

"Exosome" as used herein refers to small (30 nm to 150 nm) intracellular membrane-based vesicles that are released by cells and contain intracellular transmitters of RNA and proteins to enable intracellular communication. Exosomes are released by several cell types and carry active signals that are able to influence the activity of recipient cells.

"Secretome" as used herein refers to as collection of proteins consisting of transmembrane proteins and proteins secreted by cells into the extracellular space. Secretory proteins play important roles in cell migration, cell signaling and communication. The proteins and RNA factors in the secretome are packaged into extracellular vesicles and exosomes.

"Small molecule" as used herein refers to low molecular weight molecules that include lipids, monosaccharides, second messengers, other natural products and metabolites, as well as drugs, such as antibiotics, and other xenobiotics. Small molecules can be a small non-peptide, organic compound that is biologically active. Exemplary small molecules used in the invention include, but are not limited to, growth factors such as basic fibroblast growth factor (bFGF); endoglin inhibitors such as TRC105; lncRNAs such as MALAT1, GAS5, and linc-VLDLR; and transcriptional factors such as Sox15, Oct4, KLF4, Nanog, Sal4, and BMI1.

The term "senescence" as used herein refers to the permanent cessation of DNA replication and cell growth that is not reversible by growth factors. This phenomenon can occur at the end of the proliferative lifespan of normal cells or in normal or tumor cells in response to cytotoxic drugs, DNA damage or other cellular insult. Senescence can be characterized by certain morphological features including, but not limited to, increased size, flattened morphology, increased granularity, and senescence-associated β-galactosidase activity (SA-β-gal).

A "therapeutically effective amount" as used herein is defined as concentrations or amounts of components which are sufficient to effect beneficial or desired clinical results, including, but not limited to, altering the metabolic profile of an omental adipose cell to that of a subcutaneous adipose cell. Compositions of the present invention can be used to affect a favorable change in the condition whether that change is an improvement or a complete elimination of symptoms due to obesity. In accordance with the present invention, a suitable single dose size is a dose that can prevent or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing obesity treatment or enhancing obesity treatment without causing significant side effects or adverse reactions.

"Administration" or "administering" is used to describe the process in which small molecules, including, but not limited to, growth factors, antibiotics such as endoglin inhibitors, lncRNAs or any combination thereof of the present invention are delivered to a patient. The composition may be administered in various ways to the patient as long as the small molecules are capable of reaching the adipose cells.

The small molecules described herein can be pharmaceutical compositions formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19*th* ed.) describes formulations which can be used in connection with the subject invention.

For ease of administration, the subject compounds may be formulated into various pharmaceutical forms. As appropriate compositions, there may be cited all compositions usually employed for systemically or topically administering drugs. To prepare the pharmaceutical compositions of this invention, atranorin or other polyphenolic lichen acid isolate, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions, suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition such as a metabolic disorder.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds used in other embodiments of the present invention. Additionally, compounds used in the present invention may be administered in combination with or concurrently with other therapeutics for metabolic disorders.

Example 1

ASCs from Subcutaneous and Omental Depot Show Differences in Expression of Stem Cell Transcription Factors ASCs from white adipose tissue have tremendous potential in regenerative medicine and hence the inventors sought to characterize ASC from subcutaneous and omental adipose depots. The two depots are highly clinically relevant and have distinct functions in adipose biology. Subcutaneous adipose tissue secretes higher levels of leptin while omental fat has higher expression of lipogenic and lipolytic genes (Bortolotto J W, Reis C, Ferreira A, et al. Higher content of trans fatty acids in abdominal visceral fat of morbidly obese individuals undergoing bariatric surgery compared to non-obese subjects. Obes Surg 2005, 15:1265-70; Caserta F, Tchkonia T, Civelek V N, et al. Fat depot origin affects fatty acid handling in cultured rat and human preadipocytes. Am J Physiol Endocrinol Metab 2001, 280:E238-47). Due to the inherent differences in the adipose tissue depot, it is important to evaluate the genetic profiles of the stem cells isolated from different adipose depots. (Baglioni S, Cantini G, Poli G, et al. Functional differences in visceral and subcutaneous fat pads originate from differences in the adipose stem cell. PLoS One 2012, 7:e36569; Dusserre E, Moulin P, Vidal H. Differences in mRNA expression of the proteins secreted by the adipocytes in human subcutaneous and visceral adipose tissues. Biochim Biophys Acta 2000, 1500:88-96). In addition, the inventors sought to evaluate stem cell markers in obesity as it has been shown that obesity changes the stem cell niche. (Watson 2014; Dusserre E, Moulin P, Vidal H. Differences in mRNA expression of the proteins secreted by the adipocytes in human subcutaneous and visceral adipose tissues. Biochim Biophys Acta 2000, 1500:88-96).

The results demonstrate that stem cell markers Oct4, Sal4, Sox15, KLF4 and BMI1 had expression patterns specific to the ASC obtained from either subcutaneous or omental depots as well as between lean or obese donors. The ASC derived from the subcutaneous depot of obese donor had lower expression of Oct4, Sal4, Sox155, KLF4 but higher expression of BMI1 compared to subcutaneous depot of the lean donor. In contrast, the ASC derived from omental depot of obese donor had higher expression of Oct4, Sal4, Sox15, KLF4 and BMI1 compared to omental depot of the lean donor. These results further attest to the finding that obesity changes the adipose stem cell niche and is dependent on the depot-specific source of the ASC.

ASCs from the subcutaneous and omental depot were isolated from either a lean or an obese donor. To validate the pluripotency of the ASC, the inventors evaluated the stem cell surface antigens on the ASC from subcutaneous (sc-ASCn) and omental depot (om-ASCn) from lean subjects and ASC from subcutaneous and omental depots from obese subjects (sc-ASCo and om-ASCo) (Table 1). The results indicate that ASC from all depots were negative for CD34; CD45 was absent in the omental ASC from lean and obese donors (om-ASCn and om-ASCo) while CD105 was 10-fold higher in ASC from omental depots (om-ASCn and om-ASCo) compared to ASC derived from subcutaneous depots (sc-ASCn and sc-ASCo) of either lean or obese. Interestingly, CD106 was detected only in sc-ASCo.

TABLE 1

Comparison of stem cell antigens and markers

| Maker | Other names | sc-ASCn (%) | Om-ASCn (%) | Sc-ASCo (%) | Om-ASCo (%) |
|---|---|---|---|---|---|
| CD31 | PECAM-1 | 1.10 | 0.00 | 8.30 | 0.20 |
| CD34 | L-selectin ligand | Negative | Negative | Negative | Negative |
| CD44 | Pgp-1 | 89.10 | 91.60 | 87.90 | 96.60 |
| CD45 | LCA | 0.10 | Negative | 1.80 | Negative |
| CD73 | eNT | 88.10 | 99.70 | 89.10 | 99.50 |
| CD90 | Thy-1 | 99.40 | 99.50 | 98.50 | 99.00 |
| CD105 | Endoglin | 18.00 | 96.00 | 19.00 | 99.00 |
| CD106 | VCAM-1 | Negative | Negative | 1.10 | Negative |
| CD117 | c-Kit | 0.30 | 0.20 | 0.30 | 0.20 |

Representative scatter patterns for ASC populations using flow cytometry. Table summarizes data from flow cytometry for stem cell antigens and markers, sc-ASCn, om-ASCn, sc-ASCo and om-ASCo were analyzed using flow cytometry with antibodies as indicated for stem cell antigens. Results represent fiver separate experiments.

The inventors evaluated transcription factors that define the stem cell niche. The results (FIG. 1A) indicated that sc-ASCn had significantly higher expression of Oct4, Sal4, Sox15, KLF4 and BMI1 compared to om-ASCn. The inventors next compared the stem cell markers between the ASC derived from lean and obese donors. The results (FIG. 1B) comparing the subcutaneous depots show that sc-ASCn had higher expression levels of Oct4, Sal4, Sox15, KLF4 while sc-ASCo had higher expression of BMI1. The results (FIG. 1C) comparing the omental depots show that om-ASCo had higher expression of Oct4, Sal4, Sox15, KLF4 and BMI1 compared to om-ASCn. These results indicate that obesity changes the adipose stem cell niche.

The inventors have previously demonstrated the multipotency of ASC derived from lean and obese subjects in vitro (Carter 2013; Watson 2014). Here, the inventors verified the stem cell potential of sc-ASCn, om-ASCn, sc-ASCo and om-ASCo by differentiating them to adipocytes in vitro. Oil Red O was added to stain the lipid droplets in mature adipocytes, followed by extraction of Oil Red O by isopropanol and quantification of absorbance at 490 nM. The results (FIG. 1D) show robust lipid droplet accumulation in sc-ASCn, om-ASCn, sc-ASCo and om-ASCo adipocytes while the ASC do not show lipid accumulation.

Adipose-Derived Stem Cells (ASC) Secrete Exosomes

Exosomes serve as intracellular transmitters of RNA and proteins. The therapeutic potential of the ASC also lies in its ability to secrete factors that influence other cells. The inventors used a combination of ExoQuick™ and ExoCap™ to purify the exosomes. This enabled the inventors to distinguish between the lncRNAs in the secretome which may be present in larger vesicles and those which are present in the smaller exosomes (sizes vary between 30-150 nm depending on the source). Ultracentrifugation may also be used to isolate exosomes however; the inventors chose to utilize the ExoCap™ method for higher yield of pure exosomes for the studies. (Zubiri I, Vivanco F, Alvarez-Llamas G. Proteomic analysis of urinary exosomes in cardiovascular and associated kidney diseases by two-dimensional electrophoresis and LC-MS/MS. Methods Mol Biol 2013, 1000:209-20). Other studies have also verified that the reagent method provides higher yields and purity compared to the ultracentrifugation method. (Schageman J, Zeringer E, Li M, et al. The complete exosome workflow solution: from isolation to characterization of RNA cargo. Biomed Res Int 2013, 2013:253957).

Figure 2:
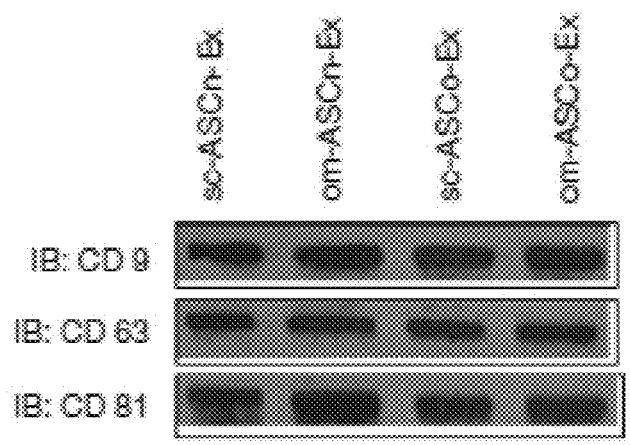
FIG. 2 is an image depicting Isolation of exosomes. (A) Exosomes were isolated and purified from sc-ASCn, om-ASCn, sc-ASCo and om-ASCo as described in methods. Western blot analysis was performed using exosome surface protein specific antibodies CD9, CD63 and CD81. Experiments were repeated four times with similar results.

Factors secreted by stem cells, also referred to as its secretome, often influence the neighboring organs. The protein and RNA factors in the secretome are packaged into extracellular vesicles and exosomes. Exosomes are the smallest vesicles in diameter and have a high therapeutic potential as its cargo can be transferred to the recipient cells where it affects gene expression. The four adipose stem cells sc-ASCn, om-ASCn, sc-ASCo and om-ASCo were grown to confluency and medium replaced with serum-free defined medium. To analyze the secretome, CM from the ASC was collected after 48 h. The extracellular vesicles were isolated from CM using ExoQuick™. Since ExoQuick™ also precipitates lipo-proteins and larger vesicles, ExoCap™ was then applied to the samples to obtain pure exosomes. ExoCap™ uses magnetic beads coated with exosome specific markers CD9, CD63 and CD81 to purify exosomes. The inventors validated the exosome preparation using western blot analysis performed with antibodies against the exosome specific markers (FIG. 2).

The inventors evaluated the concentration and sizes of the exosomes secreted from subcutaneous and omental (sc-ASCn and om-ASCn) and compared them to subcutaneous and omental ASC derived from obese donor (sc-ASCo and om-ASCo). Using nanoparticle tracking analysis from NanoSight (NTA 3.1, Build 3.1.46), the inventors observed that the size particle was physically homogeneous for each ASC exosome subtype with the sizes in the range of [90-100]±5 nm as summarized in Table 2. The exosome yield per 106 ASCs per day varied between sc-ASCn, om-ASCn, sc-ASCo and om-ASCo as shown in Table 2. The omental depots secreted larger exosomes at higher concentrations compared to the subcutaneous depots. These results indicate that exosomes, which may function as intracellular messengers, are secreted differentially into the CM by sc-ASCn, om-ASCn, sc-ASCo and om-ASCo.

TABLE 2

Nanoparticle tracking analysis from NanoSight (NTA 3.1, Build 3.1.46)

| Items | Peak diameter (nm) | Concentration (×$10^6$ mL) |
|---|---|---|
| sc-ASCn | 89 ± 7 | 1.10 ± 0.08 |
| om-ASCn | 101 ± 4 | 1.41 ± 0.04 |
| sc-ASCo | 91 ± 8 | 1.24 ± 0.09 |
| om-ASCo | 104 ± 7 | 1.49 ± 0.02 |

The Nanoparticle tracking analysis was used to analyze peak diameter (nm) and concentration of exosomes obtained from $10^6$ cells from sc-ASCn, sc-ASCo, om-ASCn and om-ASCo. Analysis repeated thrice with similar results.

LncRNA Content of Adipose-Derived Stem Cells (ASC) Exosomes

LncRNAs are important regulators of gene expression and epigenetic regulation. LncRNAs are packaged in exosomes to prevent degradation. The inventors sought to evaluate the expression of lncRNAs within the ASC and compare it to the expression levels in its secretome. Using an lncRNA array (SBITM) the inventors evaluated a spectrum of lncRNAs within the ASC and its secretome measured in the CM. The inventors isolated total RNA from ASC, CM or from exosomes from sc-ASCn, om-ASCn, sc-ASCo and om-ASCo. The analysis included only those lncRNAs which were consistently observed in the sc-ASCn, om-ASCn, sc-ASCo and om-ASCo and were statistically significant. This set included anti-NOS2a, DLG2A5, GAS5, HOTAIRM1, lincRNAp21, lincRNAVLDL, NEAT1, MALAT1. The results (FIG. 3A) indicated that the lncRNAs expression levels varied between sc-ASCn, om-ASCn, sc-ASCo and om-ASCo. Comparing the levels of lncRNAs within the ASC, the inventors observe that the expression of anti-NOS2a was seven-fold higher in om-ASCo.

Next, the inventors measured the expression of lncRNAs in the secretome (measured in CM) and compared their levels to the lncRNA expression in their respective ASC. The results show that anti-NOS2a, DLG2A5, GAS5, HOTAIRM1, lincRNAp21, lincRNA-VLDLR, NEAT1, MALAT1 are present at higher concentration in the CM. Interestingly, the inventors detected significantly higher amounts of GAS5, lincRNA-VLDLR, NEAT1 and MALAT1 in the conditioned medium (CM) compared to the corresponding ASC. GAS5 levels were predominantly increased in CM from both subcutaneous and omental depots of lean ASC; while NEAT1 and MALAT1 were significantly higher in CM from omental depot of obese ASC.

The inventors evaluated the expression of these lncRNAs within the exosomes. The results (FIG. 3B) indicate that GAS5, lincRNA-VLDLR and MALAT1 are enriched in the exosomes while anti-NOS2a, DLG2A5, HOTAIRM1, lincRNAp21, NEAT1 are not detected in the exosomes from CM of sc-ASCn, om-ASCn, sc-ASCo and om-ASCo. The results further show that lincRNA-VLDLR expression is highest in exosomes isolated from CM of om-ASCo and MALAT1 expression is highest in exosomes isolated from CM of sc-ASCn.

The results indicated that lincRNA-VLDLR, GAS5 and MALAT1 are enriched in the exosomes and this may suggest that they function as intra-cellular messengers. The very low expression of anti-Nos2a, DLG2A5, HOTAIRM1, NEAT1 and lincRNAp21 in the exosome preparations may suggest that these lncRNAs are packaged in larger secretory vesicles. The results indicate that exosomes from sc-ASCn, the predominately used ASC source in regenerative medicine, is enriched in MALAT1.

Interestingly, NEAT1 expression is significantly elevated in om-ASCo-CM compared to om-ASCo. The results suggest that extracellular vesicles from the secretome of obese ASC could also be used in therapeutic applications or to decipher disease state mechanisms. Karastergiou et al. showed expression of homeobox genes from abdomen or gluteal depot in the adipose tissue as well as in the stromal cells. (Karastergiou K, Fried S K, Xie H, et al. Distinct developmental signatures of human abdominal and gluteal subcutaneous adipose tissue depots. J Clin Endocrinol Metab 2013, 98:362-71)

The differential expression of these genes contributed to the distinct phenotypic characteristics of peripheral fat. The inventors limited the study to evaluation of lncRNAs observed consistently in sc-ASCn, om-ASCn, sc-ASCo and om-ASCo. Additional analysis using RNAseq provides an exhaustive list of all RNA including miRNAs, mRNAs, lncRNAs and other non-coding RNAs present in the exosomes derived from sc-ASCn, om-ASCn, sc-ASCo and om-ASCo.

The inventors found that the size and concentration of exosomes secreted from omental depots of lean or obese ASC are higher compared to those secreted from subcutaneous depots of lean or obese ASC. Importantly, the inventors show that their lncRNA content varies significantly between ASC, its secretome and the cargo contained within the exosomes.

Senescence and Obesity

In obesity, the omental fat is infiltrated by immuneinflammatory cells and is implicated in metabolic syndrome to a higher extent compared to subcutaneous fat. Cellular senescence evolved as a means to prevent hyperproliferation of dysfunctional cells. The inventors previously showed that the stem cell niche is altered in obesity and expression of PKCδ, a kinase mediating cellular proliferation, differentiation and apoptosis, is higher in obese adipocytes compared to lean adipocytes. (Carter 2013). Senescence in mature adipocytes and adipose tissue has been studied earlier with reports indicating that adipose tissue upon aging accumulates senescent cells in WAT and causes age-associated morbidity. (Shen X, Du Y, Shen W, et al. Adipose-derived stem cells promote human dermal fibroblast function and increase senescence-associated β-galactosidase mRNA expression through paracrine effects. Mol Med Rep 2014, 10:3068-72; Mantovani C, Terenghi G, Magnaghi V. Senescence in adipose-derived stem cells and its implications in nerve regeneration. Neural Regen Res 2014, 9:10-5; Jun H S, Dao L T, Pyun J C, et al. Effect of cell senescence on the impedance measurement of adipose tissue-derived stem cells. Enzyme Microb Technol 2013, 53:302-6; Markowski D N, Thies H W, Gottlieb A, et al. HMGA2 expression in white adipose tissue linking cellular senescence with diabetes. Genes Nutr 2013, 8:449-56).

In the current example, the inventors sought to evaluate senescence in ASC and compare the number of senescent cells in ASC from lean and obese. The results demonstrated that lean ASC from subcutaneous and omental depots have higher senescent cells compared to obese ASC depots. This result suggests that the obese cells have undergone an epigenetic modification to promote hyperproliferation. It is reported that SA-RNA-1 lncRNA is associated with senescence and levels of lncRNAs change with senescence. (Abdelmohsen K, Panda A, Kang M J, et al. Senescence associated lncRNAs: senescence-associated long noncoding RNAs. Aging Cell 2013, 12:890-900). Obesity is characterized by hyperplasia and hypertrophy which may be influenced by the altered stem cells niche. PKCδ modulates cellular senescence by mediating a cascade of mitogenic signals. (Katakura Y, Udono M, Katsuki K, et al. Protein kinase C delta plays a key role in cellular senescence programs of human normal diploid cells. J Biochem 2009, 146:87-93; Byun H O, Jung H J, Kim M J, et al. PKCδ phosphorylation is an upstream event of GSK3 inactivation-mediated ROS generation in TGF-β1-induced senescence. Free Radic Res 2014, 48:1100-8). The experiments with PKCδ silencing in the ASC showed an increase in cellular senescence in obese ASC in both subcutaneous and omental depots. These results suggest that PKCδ regulates cell cycle arrest in senescent cells and modulating its expression may influence the stem cell niche in adipose tissue and obesity. The inventors previously showed that PKCδ regulates cell cycle in differentiating mouse pre-adipocyte 3T3L1 cell line. (Patel R S, Carter G, Cooper D R. et al. Transformer 21 homolog (*Drosophila*) (TRA2B) regulates protein kinase C δI (PKCδI) splice variant expression during 3T3L1 preadipocyte cell cycle. J Biol Chem 2014, 289:31662-72).

Senescence in Adipose-Derived Stem Cells (ASC)

Figure 4:
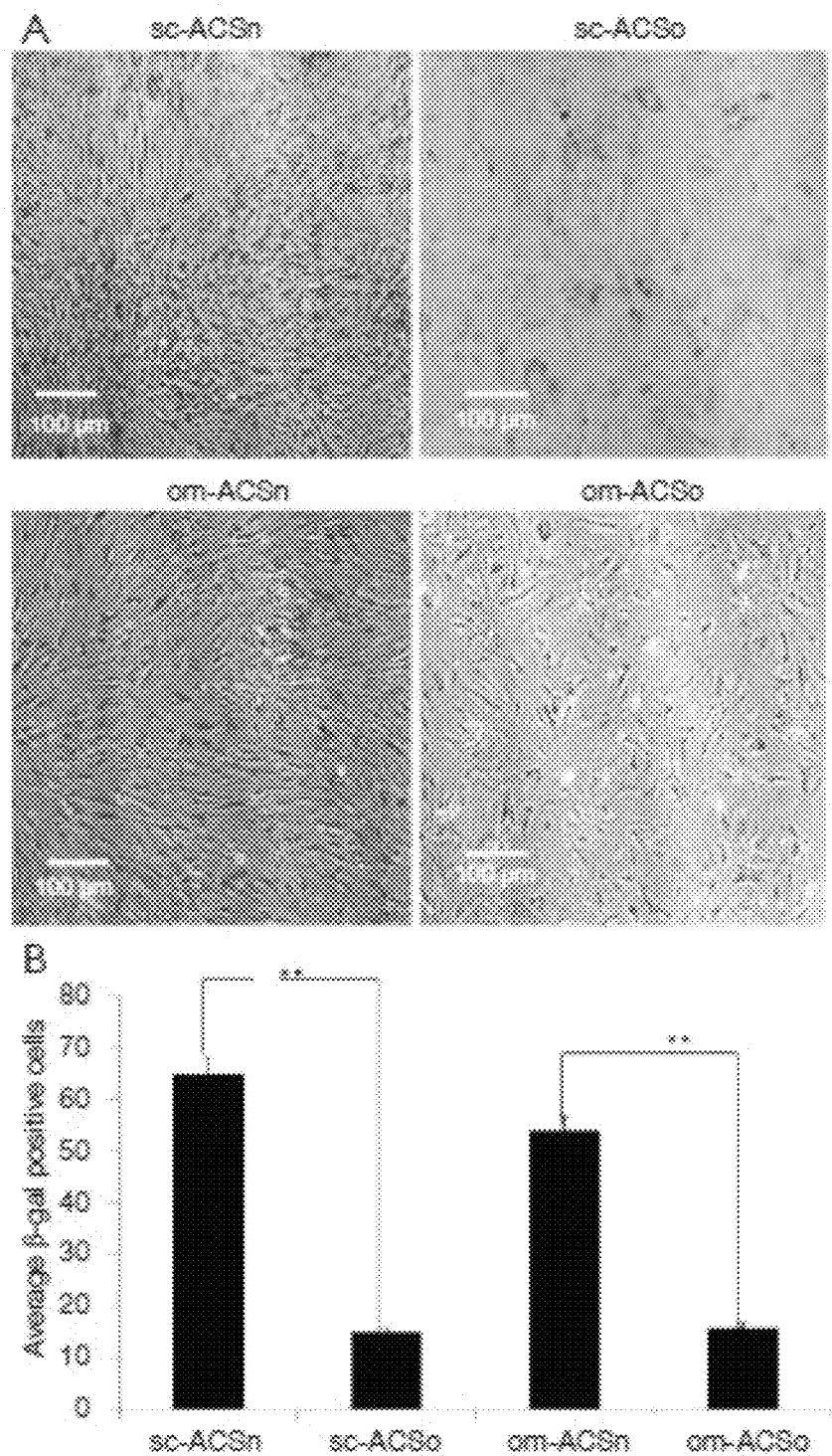
FIG. 4A-B is a series of images depicting Senescence in ASC. (A) sc-ASCn, om-ASCn, sc-ASCo and om-ASCo were stained for β-galactosidase to detect senescence. Cells were then visualized under 4× light microscopy using Nikon Eclipse microscope. The percent of cells staining positive was calculated by counting five areas of the same size from each field per sample using NIS elements advance research image tool software. (B) The graphs show average of β-gal positive cells. Statistical analysis performed by two-tail Student's t-test. **, $P<0.01$.

Adipose stem cells tightly regulate their self-renewal capacity and ability to differentiate and commitment duality. Obesity is often associated with senescence. Normal cells remain quiescent and obesity or other disease states amplify the ASC to differentiate and exit the senescence stage. The inventors determined the senescence-associated (S A) β-galactosidase activity by visualizing it as a blue stain in cells. The inventors evaluated the senescent state of subcutaneous and omental ASC from lean and obese donors. The results show that senescence is decreased in both sc-ASCo and om-ASCo obese cells (FIG. 4) compared to sc-ASCn and om-ASCn.

PKCδ Expression in Adipose-Derived Stem Cells (ASC)

Figure 5:
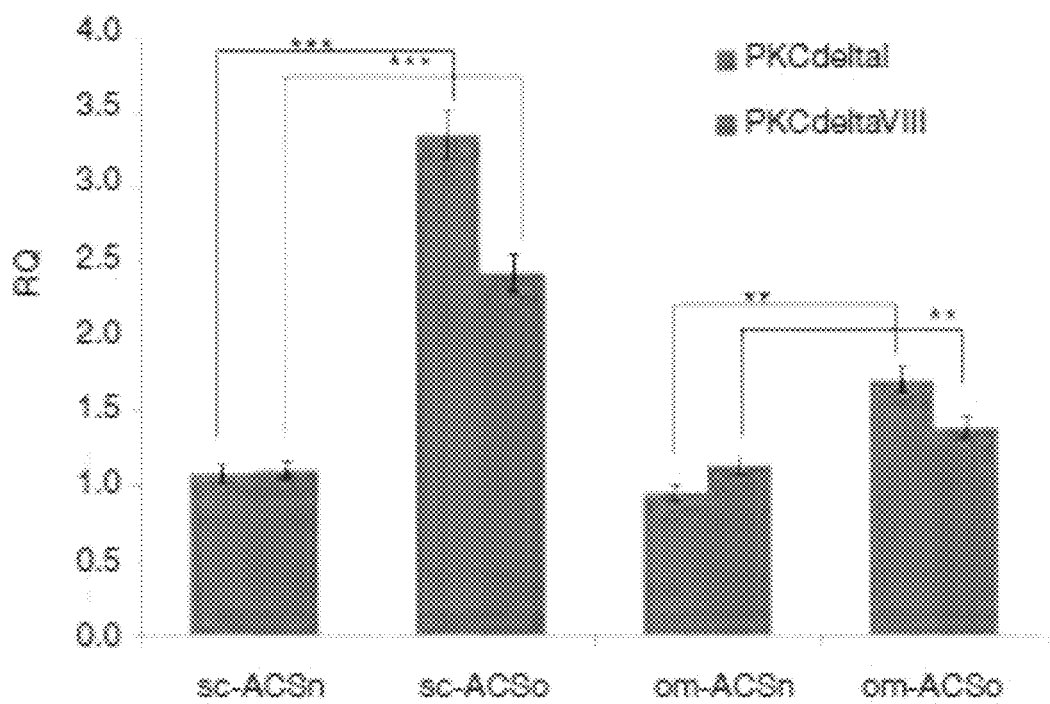
FIG. 5 is a graph depicting Expression of PKCδI and PKCδVIII in ASC. Total RNA was isolated form sc-ASCn, om-ASCn, sc-ASCo and om-ASCo. Real time qPCR was used to measure expression of PKCδ alternatively spliced variants PKCδI and PKCδVIII. The graph shows relative quantification (RQ). The experiment was independently repeated five times with similar results. Statistical analysis performed by two-way analysis of variance; , P<0.01; *, P<0.001.

PKCδ is implicated in the regulation of transcription factors which maintain the stem cell niche (Hamdorf 2011; Lee, 2010). Hence, the inventors evaluated the expression of PKCδ in sc-ASCn, om-ASCn, sc-ASCo and om-ASCo. The results showed that both alternatively spliced products of human PKCδ: PKCδI and PKCδVIII were increased in sc-ASCo and om-ASCo derived from obese donor compared to sc-ASCn and om-ASCn (FIG. 5) derived from lean donor.

Figure 6A:
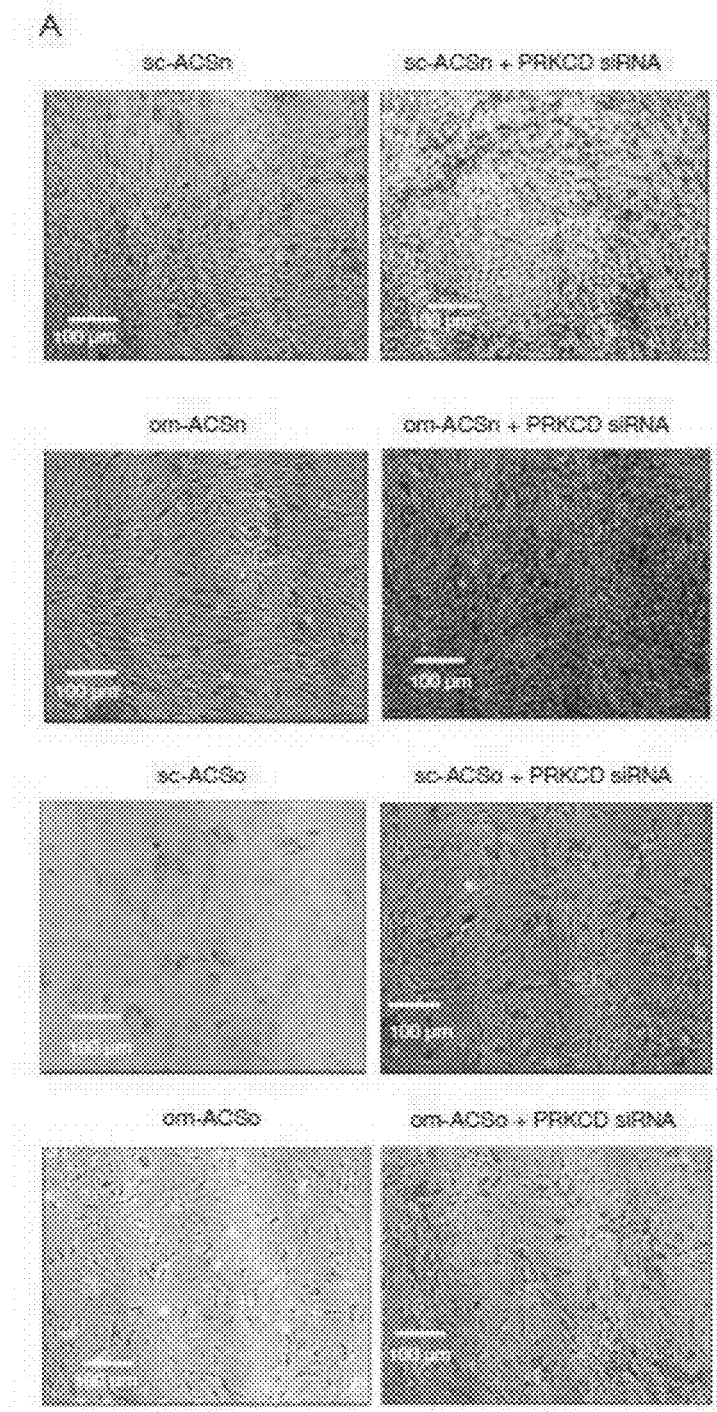

Effect of PRKCD Silencing on Adipose-Derived Stem Cells (ASC) Markers and Senescence PKCδ regulates mitogenic signals to regulate a cascade of molecular events underlying senescence (Katakura Y, Udono M, Katsuki K, et al. Protein kinase C delta plays a key role in cellular senescence programs of human normal diploid cells. J Biochem 2009, 146:87-93). The results above showed that PKCδ was increased in obese ASC. To evaluate its effect on senescence in ASC, PKCδ expression was knocked down using PRKCD siRNA which silences both PKCδI and PKCδVIII. The results indicated an increased number of senescent cells in both sc-ASCo and om-ASCo. Further, the results demonstrate that in om-ASCn transfected with PRKCD siRNA, the percent of senescent cells observed doubled compared to om-ASCn (FIG. 6A-C).

The inventors further evaluated the expression of stem cell markers after PRKCD siRNA treatment. The results (FIG. 6D) show that Oct4, KLF4 and BMI1 were up-regulated with PRKCD knockdown in sc-ASCn, om-ASCn, sc-ASCo and om-ASCo. This suggested that PKCδ may regulate the expression of transcription factors which are important in maintaining the stem cell niche.

Materials and Methods:

Adipose Samples

White adipose tissue was obtained as discarded tissue from surgeries performed at Tampa General Hospital by Dr. Murr. Donors consented to their waste tissue to be used in research. The subcutaneous and omental depots were collected from the same subject. The lean adipose tissue samples were obtained from a female donor with BMI of 21.3 and the obese adipose tissue samples were from a female donor with BMI of 54.6. Both subjects were non-diabetic, non-smokers and did not have any form of cancer. The de-identified samples were obtained under an Institutional Review Board approved protocol (University of South Florida IRB #20295) with a "not human research activities determination" and was transported to the laboratory and processed within 24 h of collection.

Adipose-Derived Stem Cells (ASCs)

ASC were isolated as previously described by the lab in Watson 2014. Briefly, adipose tissue was cut up into small pieces and digested with 0.075% collagenase type 1 (Worthington) in modified PBS for 2 h at 37° C. The digestion was stopped by adding α-MEM +20% heat-inactivated FBS. The suspension was filtered and centrifuged at 400 g at room temperature. The pellet contains the SVF. The pellet was resuspended in 1 mL of the erythrocyte lysis buffer (stem cell technologies) for 10 min and washed in 20 mL of PBS with 2% P/S/A before centrifugation, 300-500 g, 5 min. The supernatant was aspirated and the cell pellet resuspended in a 3 mL stromal medium (α-MEM; Mediatech, Mannassas, Va.) with 20% FBS, 1% 1-glutamine (Mediatech), 1% P/S/A. Following three rinses in the stromal medium, SVF cells were plated for initial cell culture at 37° C. with 5% CO2 in ASC medium from ZenBio™ (Cat# PM-1). Sub-confluent cells were passaged by trypsinization. Experiments were conducted within passages 2-3.

In Vitro Differentiation of Adipose-Derived Stem Cells (ASC) to Adipocytes

The ASC lines were tested in culture to differentiate into mature adipocytes and show accumulation of lipid and secrete adiponectin and leptin. At the start of all experiments, cells were grown to confluency such that all cells are synchronized and then differentiated. The cells were cultured as follows. ASC were passaged with preadipocyte medium (PM-1; DMEM/Ham's F-12 medium, HEPES, FBS, penicillin, streptomycin, amphotericin B; ZenBio™) and then plated at 50,000 cells/cm2 with PM-1. Cells were fed every other day with PM-1 until confluent. To induce differentiation, PM-1 medium was replaced with differentiation medium (DM2; ZenBio™) which included biotin, pantothenate, human insulin, dexamethasone, isobutylmethylxanthine and a PPARγ agonist (days 0-7). After 7 days, DM-2 medium was replaced with Adipocyte Medium (AM1; ZenBio™; days 7-14), which included PM-1, biotin, pantothenate, human insulin and dexamethasone. By day 14, cells contained large lipid droplets and were considered mature adipocytes. Cells were maintained at 37° C. in a humidified 5% CO2 atmosphere.

Adipocyte Size

Adipocytes were differentiated in 100 mm plate and their sizes determined on day 14 (i.e. of mature adipocytes). Maximal diameter of 10 adjacent adipocytes from 6 different fields was calculated using Nikon Eclipse inverted microscope and NIS elements advance research image tool software. The data was transferred to excel to calculate the mean diameter and standard deviation. This was repeated in three separate experiments to ensure reproducibility.

Apoptosis Assay

Human preadipocytes were cultured on 60 mm dishes as described in methods. For apoptosis assays, cells were serum-starved for 48 hours. Media was collected and cells were washed one time with HBSS and then trypsinized for 5.0 minutes. Five ml complete media was added to neutralize the trypsin. Media and washes were pooled and centrifuged at 1200 RPMS for five minutes. Cells were washed one time with PBS and one time with binding buffer and then incubated for 15 min with 5.0 ul AV-FITC and 5.0 ul PI in 100 ul binding buffer (BD Pharmagen, San Diego, Calif.) at room temperature in the dark. 400 ul binding buffer was added and cells were analyzed by flow cytometry within one hour. Annexin V-FITC and PI fluorescence were measured using an Accuri C6 flow cytometer.

Exosome Isolation

The four adipose stem cells sc-ASCn, om-ASCn, sc-ASCo and om-ASCo were grown to confluency and the medium was replaced with serum-free mesenchymal stem cell basal medium (MSC-BM-CD from Lonza #00190620). Conditioned media (CM) was collected from the ASC after 48 h and centrifuged at 3,000 g for 15 min to remove dead cells. ExoQuick™ (SBI) reagent was added to the CM and incubated overnight at 4° C. Following centrifugation at 1,500 g for 30 min, the pellet was further processed. ExoCap™ (JSR Life Sciences) composite reagent containing magnetic beads for CD9, CD63 and CD81 was used to purify exosomes. Exosomes were eluted from beads using the manufacturer's elution buffer and used in western blot analysis or in qPCR.

Western Blot Analysis

Protein lysates were obtained from the ASC using lysis buffer containing protease inhibitors. The lysates (40 μg) were separated by SDS-PAGE with 10% gels, electrophoretically transferred to nitrocellulose membranes, blocked with Tris-buffered saline containing 0.1% Tween 20 and 5% nonfat dried milk, washed, and incubated with antibody specific for CD9, CD63 or CD81 (cell signaling). After incubation with anti-rabbit IgGHRP, enhanced chemiluminescence (Pierce) was used for detection. The blots were analyzed on ProteinSimple Fluor M and Alpha View™ software was used for densitometric analysis.

SiRNA Transfection

PRKCD siRNA (ID: 103702) and scrambled siRNA were purchased from Thermo Fisher Scientific. This siRNA was previously validated for specificity and off-target gene effects were eliminated. The 50 nM of PRKCD siRNA or scrambled siRNA was transfected in ASC for 48 hours using siPORT NeoFX® transfection agent. Total RNA was harvested and used as described in experiments.

Quantitative Real-Time qPCR

Total RNA was isolated from ASC using RNAzol according to the manufacturer's protocol (TelTest Inc., Friendswood, Tex.). The 2 μg RNA was reverse-transcribed with Omniscript R kit (Qiagen) using oligo dT primers. QPCR was performed using 1.0 μL cDNA and Maxima SYBR Green/Rox qPCR master mix (Thermo Scientific). The primers for the stem cell transcription factors are:

Oct4 sense: 5'-TCCCATGCATTCAAACTGAGG-3' (SEQ ID NO: 1) and antisense 5'-CCAAAACCCTGGCA-CAAACT-3' (SEQ ID NO:2);

Sal4 sense: 5'-GCCCAGATATCCTGGAAACCA-3' (SEQ ID NO:3) and antisense 5'-TTCTCGGAGCTCTCT-TGCTTTG-3' (SEQ ID NO:4);

Sox15 sense: 5'-GAACAGGTTGGAAGCAAAGGC-3' (SEQ ID NO:5) and antisense 5'-GAACAGGTTG-GAAGCAAAGGC-3' (SEQ ID NO:6);

KLF4 sense: 5'-CTGCGGCAAAACCTACACAA-3' (SEQ ID NO:7) and antisense 5'-GGTCGCATTTTTG-GCACTG-3' (SEQ ID NO:8);

BMI1 sense: 5'-AATGTCTTTTCCGCCCGCT-3' (SEQ ID NO:9) and antisense 5'-ACCCTCCACAAAGCACAC-CACAT-3' (SEQ ID NO: 10);

PKCδVIII sense: 5'-TGGGTCCATTGCCCCATTAC-3' (SEQ ID NO: 11) and antisense 5'-CGTAGGTCCCACT-GTTGTCC-3' (SEQ ID NO:12);

PKCδI sense: 5'-ACATCCTAGGTA-CAACAACGGGAC-3' (SEQ ID NO:13) and antisense 5'-ACCACGTCCTTCTTCAGACAC-3' (SEQ ID NO: 14).

Amplification was performed on the ViiaA 7 (Applied Biosystems). Real-time PCR was then performed in triplicate on samples and standards. The plate setup included a standard series, no template control, no RNA control, no reverse transcriptase control, and no amplification control. After primer concentrations were optimized to give the desired standard curve and a single melt curve, relative quotient (RQ) was determined using the ΔΔCT method with U1RNA as the endogenous control and sc-ASCn as the calibrator sample. The long noncoding RNAs (lncRNAs) array was purchased from SBI (catalog #RA910-A1) and includes cDNA master mix and SYBR Green master mix for real time qPCR. Experiments were repeated four times.

Flow Cytometry

Immunophenotypical analysis of cultured cells was performed using FITC-, PE-, or APC conjugated monoclonal antibodies against CD31, CD34, CD44, CD45, CD73, CD90, CD105, CD106, and CD117. Cells were detached using the EDTA buffer, washed, and resuspended at a concentration of 106 cells/mL. Cells were incubated at 4° C. for 10 min in PBS with 10% FBS and centrifuged for 5 min at 200 g. The cell pellet was resuspended in the binding buffer (PBS/2% FBS/0.01% sodium azide) followed by incubation with the specific antibodies at 4° C. for 30 min, then washed with the binding buffer, and resuspended in 0.5 mL of the same buffer and analyzed by flow cytometry (BD Accuri C6).

Senescence

ASC were grown in 60 mm plates. Cells were washed with 1×PBS and fixed with 1× fixative solution (20% formaldehyde, 2% glutaraldehyde in 10×PBS) for 15 min at room temperature. Cells were rinsed and 1 mL of β-galactosidase staining solution (400 mM citric acid/sodium phosphate, 1.5 M NaCl, 20 mM MgCl2, 500 mM potassium ferrocyanide and 20 mg/mL X-gal in DMF) was added to cells and incubated overnight in a dry incubator. The images were captured brightfield on a Nikon Eclipse fluorescent microscope using 4× or 10× objective with 0.38/μM pixel.

Statistical Analysis

Analyses were performed using PRISM™ software and analyzed using two-tailed Student's t-test. P<0.05 was significant; P<0.01 was highly significant; P<0.001 was extremely significant. Analysis was performed either within group or between groups as determined by the experiment.

Conclusion

In conclusion, the inventors have characterized the stem cell markers in ASCs isolated from different depots from a lean and an obese donor. The inventors evaluated the secretome and exosomes secreted by ASC and show that specific lncRNAs are enriched in the exosomes which may be transferred to recipient cells to regulate gene expression. Importantly, the inventors show that the exosome content varies between depots and between lean and obese phenotype. Finally, the inventors demonstrate that levels of senescent cells are higher in sc-ASCn and om-ASCn. PKCδ modulates senescence in ASC and it may be through the phosphorylation of transcription factors Oct4, KLF4 or BMI1. Additional molecular manipulations are needed to decipher the mechanisms underlying phosphorylation by PKCδ in ASC. These results have significant implications in understanding the adipose stem cell niche in the field of obesity. In addition, the results shed light on understanding the impact of obesity on diseases such as cancer and endocrine disorders via their exosome content which serve as intra-cellular messengers.

Example 2

Figure 7:
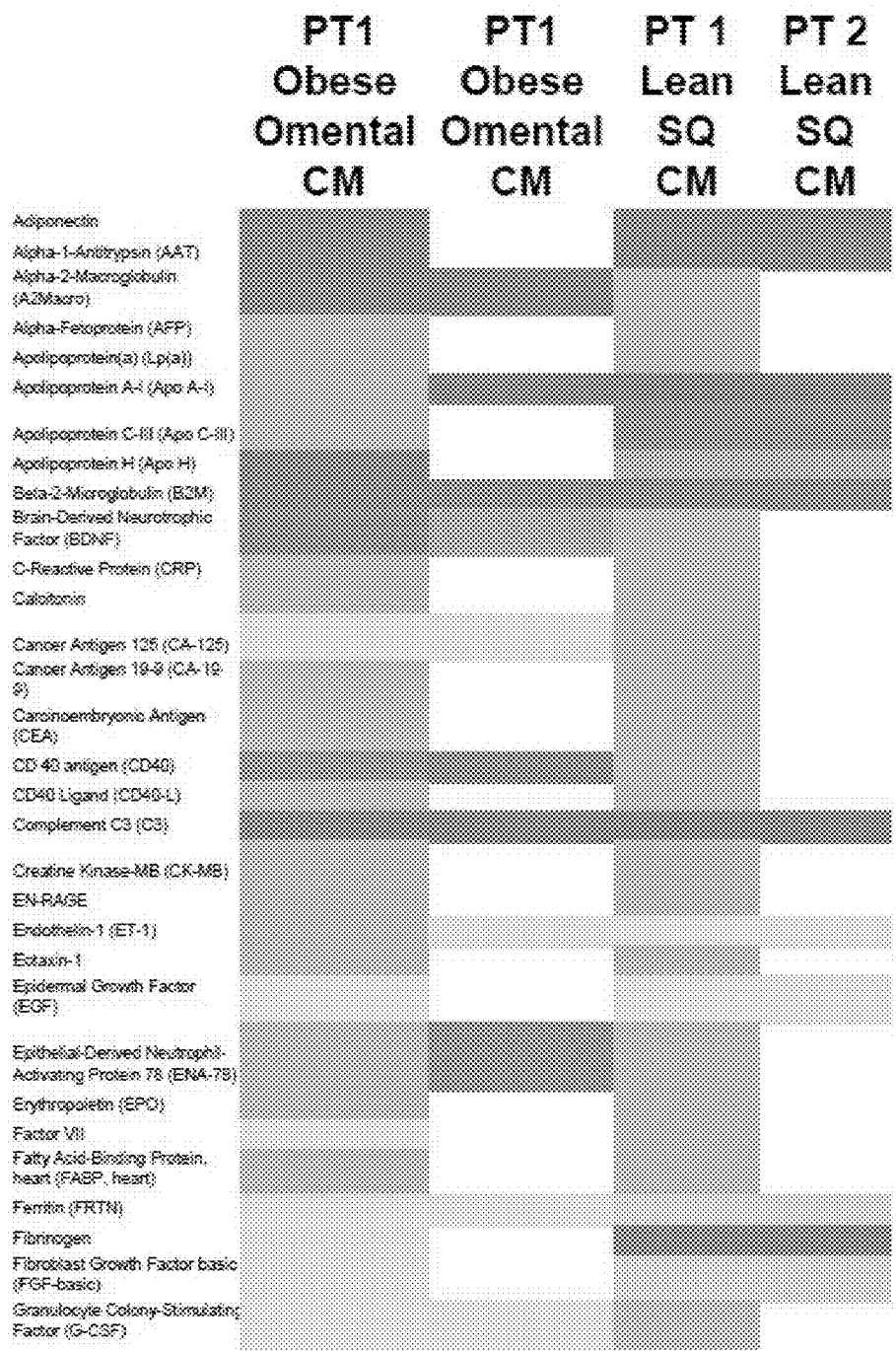
FIG. 7 is an image depicting a Heat map (Red-yellow-green) represent low to high expression levels of the secretome analytes. Real time qPCR; om-ASCo set as reference, N=3
Figure 7:
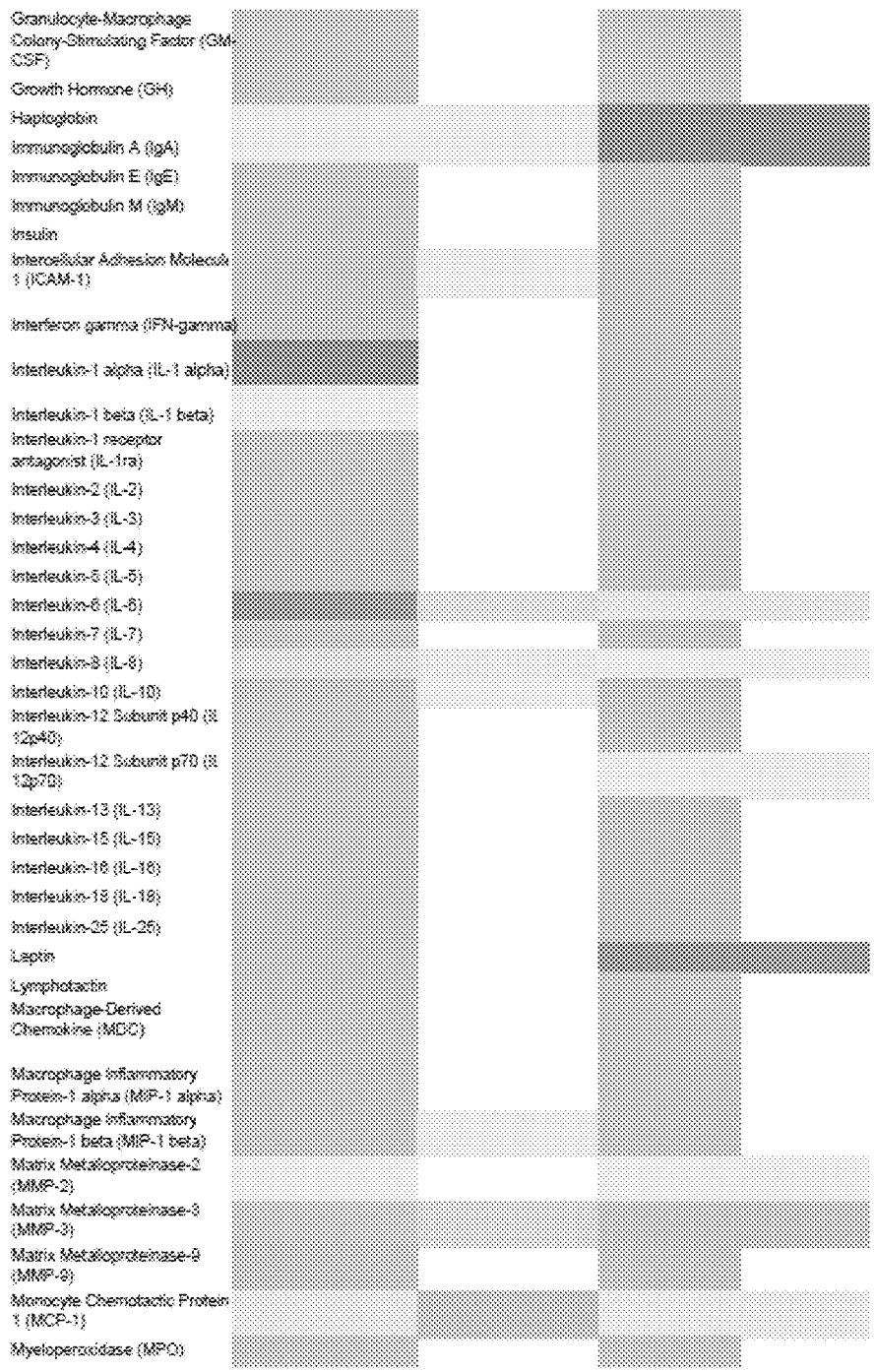

Secretome Analysis of Sc-ASCn and Om-ASCo:

Previous studies performed by the lab and other groups indicate that the omental (Om) adipose tissue contributes significantly to increase the risks of developing obesity related comorbidities, such as diabetes, cardiovascular diseases and metabolic syndrome, while subcutaneous (Sc) fat constitutes a protective factor against the same conditions. In light of these findings, the inventors evaluated their secretomes. Omental and subcutaneous abdominal adipose tissue from 4 lean and 4 obese patients (IRB#20295; obese BMIs between 43 and 45; lean BMIs between 22 and 23; non-diabetic, nonsmokers, other criteria matched), were digested with collagenase and purified. Briefly, the pellet is the stromal vascular fraction which contains ASC while the supernatant contains adipocytes. ASC are purified with FACS to obtain pure ASC (free from other cells and macrophages). ASC are maintained in pre-adipocyte media (ZenBio™) for 48 h and to evaluate their secretome conditioned media (CM) was collected. The inventors used the multi-analyte platform (MAP) from MyriadRBM for a comprehensive, quantitative assay for cytokines, chemokines, metabolic markers, hormones, growth factors, tissue remodeling proteins, angiogenesis markers, and circulating proteins (total 90 analytes; HumanMAP v1.6) (FIG. 7 representing 2 lean or obese patients; n=4). A significant difference was observed in bFGF levels which were higher in sc-ASCn secretome (green bar on heat map). Other differences, as predicted, were apparent in the interleukins and MCP patterns.

Sc-ASCn Secretome Affects Om-ASCo:

This secretome analyte data taken together with Example 1 data showing differences in surface markers/antigens, transcription factors and long non-coding RNAs (lncRNAs) not only between omental and subcutaneous fat, but also between obese and lean fat, reveal significant genetic variations in the adipose-derived stem cells (ASC) when comparing subcutaneous (Sc) vs. omental (Om) and lean vs. obese, which led the inventors to evaluate the impact of the micro-environment on ASC development and differentiation. The inventors evaluated whether the observed differences in the secretome of subcutaneous lean ASC (sc-ASCn) could influence the omental obese ASC (om-ASCo) into differentiating differently into a subcutaneous-like cell. Conditioned media (CM) was collected from sc-ASCn and exosomes were isolated as per methods described herein. Additionally, CM was collected from mature lean Sc adipocytes (sc-Ad) and exosomes were isolated. Briefly, CM is spun down to remove debris, ExoQuick added for 18 h. The pellet is purified using ExoCap magnetic beads (targeting tetraspanins) which capture CD9, CD63, CD81 positive exosomes. CM 50% v/v or exosomes (10 µg) from sc-ASCn or sc-Ad were added to om-ASCo for 72 h. The om-ASCo cells were collected and the genetic profile of om-ASCo cells thus treated was generated using SYBR Green Real Time qPCR. The data indicates that that CM from sc-ASCn significantly changed the expression of the transcription factors of om-ASCo thereby changing its genetic profile to reflect sc-ASCn stem cell transcription profile. Importantly, exosomes from sc-ASCn showed a significant effect while the CM and exosomes from sc-Ad did not alter the genetic profile of om-ASCo.

Omental fat is correlated to glucose intolerance, insulin resistance, hepatosteatosis, as well as in ectopic fat distribution in cardiac, skeletal and hepatic tissue significantly contributing to metabolic dysfunction. In contrast, subcutaneous fat often serves as a protective depot against the comorbidities of obesity. Hence, the inventors sought to modify the micro-environment of omental obese ASC such that it differentiates into a lean subcutaneous-like phenotype. The preliminary data showed sc-ASCn secretome changes the genetic profile of om-ASCo. The previous study characterized the genetic profiles of the two depots in lean and obese subjects. The inventors sought to reprogram the omental obese ASC using a chemical cocktail approach to introduce small molecules that convert om-ASco into functional subcutaneous-like adipocytes with an improved adipose tissue function thus engineering a therapeutic method that modifies the obese omental depot structure and function, eliminating its disease promoting capacity while maintaining normal functionality.

Materials and Methods

To maintain reproducibility, human lean and obese (Sc and Om) ASC are purchased from ZenBio™ (with rigorous quality control measures including pure populations; performance in lipid accumulation, lipolysis, adipokine secretion) and differentiated in vitro to mature adipocytes. These adipocytes closely mimic adipocyte data obtained from patients as described previously by the inventor's lab and others (Patel R S, Carter G, Bassit G E, Patel A A, Cooper D R, Murr M, Patel N A. Adipose-derived stem cells from lean and obese humans show depot specific differences in their stem cell markers, exosome contents and senescence: Role of Protein Kinase C delta (PKCδ) in adipose stem cell niche. Stem Cell Investigations. 2016, 3(1); Carter G, Apostolatos A, Patel R, Mathur A, Cooper D, Murr M, Patel N A. Dysregulated Alternative Splicing Pattern of PKC during Differentiation of Human Preadipocytes Represents Distinct Differences between Lean and Obese Adipocytes. ISRN Obesity. 2013, 2013:9; J E W, Patel N A, Carter G, Moor A, Patel R, Ghansah T, Mathur A, Murr M, Bickford P, Gould L, Cooper D R. Comparison of markers and functional attributes of human adipose derived stem cells and dedifferentiated adipocyte cells from subcutaneous fat of an obese diabetic donor. Advances in Wound Care. 2013; WOUND-2013-0452.R1 (September 2013); Carter G, Patel R S, Apostolatos A, Murr M, Cooper D R, Patel N A. Protein kinase C delta splice variant modulates senescence via hTERT in adipose derived stem cells. Stem Cell Investigations. 2014; 1(3). Epub January 2014; Cawthorn W P, Scheller E L, MacDougald O A. Adipose tissue stem cells meet preadipocyte commitment: going back to the future. Journal of lipid research. 2012; 53(2):227-46. Epub 2011/12/06; Shi J G, Fu W J, Wang X X, Xu Y D, Li G, Hong B F, Hu K, Cui F Z, Wang Y, Zhang X. Transdifferentiation of human adipose-derived stem cells into urothelial cells: potential for urinary tract tissue engineering. Cell and tissue research. 2012; 347(3):737-46).

Figure 3:
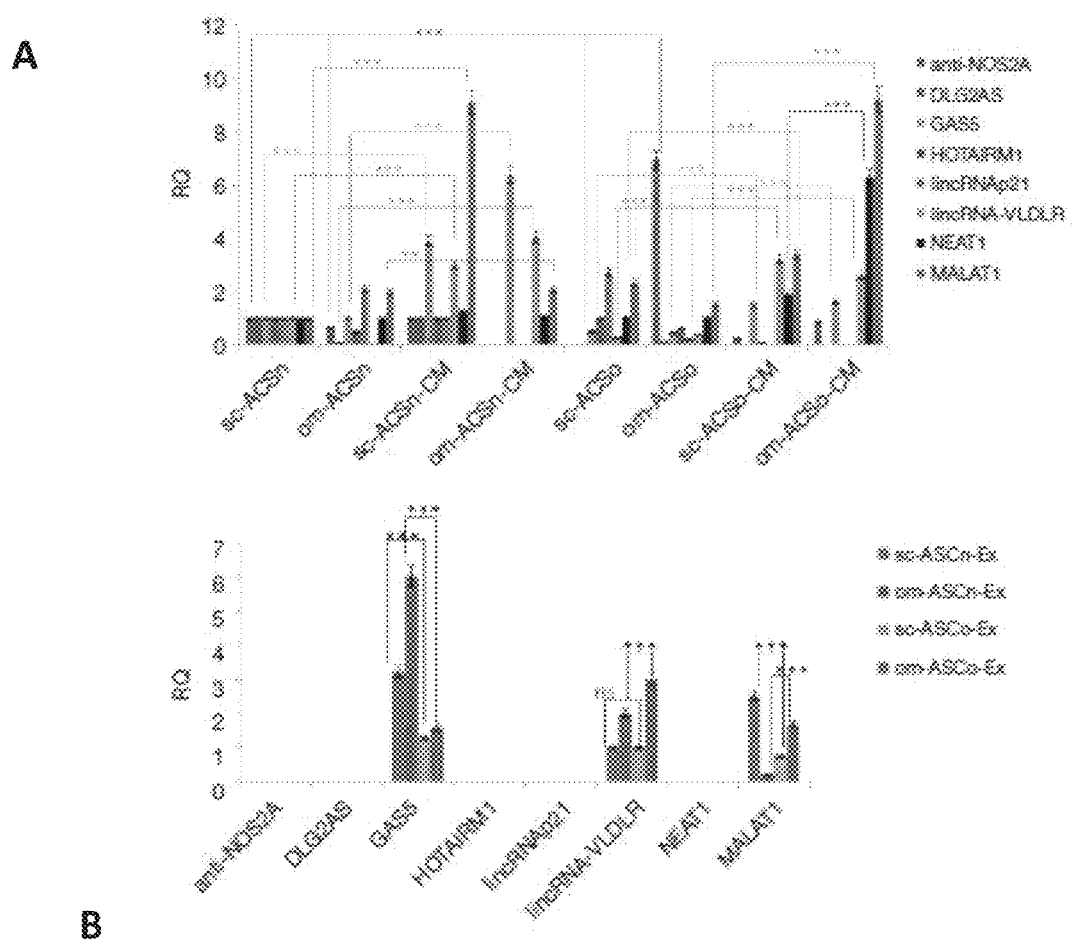
FIG. 3A-B is a series of images depicting Identification of lncRNAs in cell, conditioned media and exosomes. (A) Total RNA was isolated form sc-ASCn, om-ASCn, sc-ASCo and om-ASCo and its respective conditioned media. Real time qPCR was used to measure expression of anti-NOS2A, DLG2AS, HOTAIRM1, lincRNAp21, lincRNA-VLDLR and MALAT1. GAPDH and 18S RNA were used to normalize the data. The graph shows relative quantification (RQ) with sc-ASCn sample set as reference. Statistical analysis performed by two-way analysis of variance. The experiments were independently repeated five times with similar results. (B) LncRNAs in exosomes. Exosomes were purified from conditioned media and RNA was used in real time qPCR analysis to measure expression of anti-NOS2A, DLG2AS, GAS5, HOTAIRM1, lincRNAp21, lincRNA-VLDLR and MALAT1. The graph shows RQ. The experiment was independently repeated five times with similar results. Statistical analysis performed by two-way analysis of variance between samples as indicated in graphs. , $P<0.01$; *, $P<0.001$.
Figure 8:
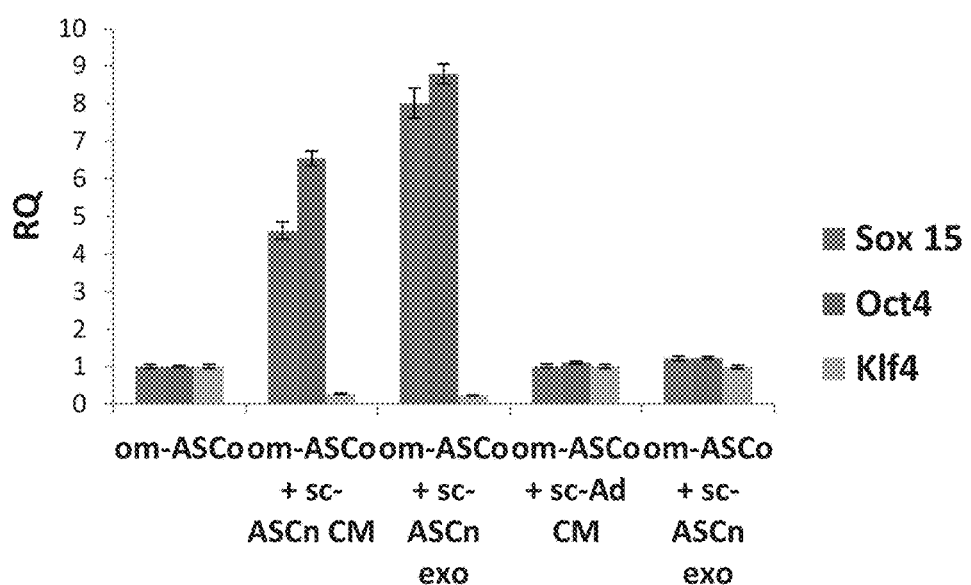
FIG. 8 is a graph depicting the secretome (CM and exosomes) of sc-ASCn significantly altered the stem cell transcription factor expression in om-ASCo.

The inventors have previously characterized om-ASCo and sc-ASCn using a transcriptomics approach as well as analyzed their secretome (Myriad R B M) shown in FIG. 7. (Patel R S, Carter G, Bassit G E, Patel A A, Cooper D R. Murr M, Patel N A. Adipose-derived stem cells from lean and obese humans show depot specific differences in their stem cell markers, exosome contents and senescence: Role of Protein Kinase C delta (PKCδ) in adipose stem cell niche. Stem Cell Investigations. 2016; 3(1)). The data analyzing the proteomic constitution of sc-ASCn secretome showed elevated levels of basic Fibroblast Growth Factor (bFGF) compared to secretome of om-ASCo. The preliminary data (FIG. 8) demonstrated that the secretome (CM and exosomes) of sc-ASCn significantly altered the stem cell transcription factor expression in om-ASCo. The previous transcriptomic profiling demonstrated that long noncoding RNAs (lncRNAs) MALAT1, GAS5, linc-VLDLR were higher in sc-ASCn secretome and that its exosomes were enriched in these lncRNAs (FIG. 3B). LncRNAs regulate gene expression, epigenetic modification, transcription and splicing of genes. The stem cell antigen marker CD105 (Endoglin) was markedly increased in the om-ASCo. Endoglin is a receptor for TGFβ and bone morphogenetic protein. Inhibition of TGFβ/Smad protects mice from obesity. TRC105 is an antibody that binds and inhibits endoglin. (Yadav H, Quijano C, Kamaraju A K, Gavrilova O, Malek R, Chen W, Zerfas P, Zhigang D, Wright E C, Stuelten C, Sun P, Lonning S, Skarulis M, Sumner A E, Finkel T, Rane S G. Protection from obesity and diabetes by blockade of TGF-beta/Smad3 signaling. Cell metabolism. 2011, 14(1):67-79; Karzai F H, Apolo A B, Cao L, Madan R A, Adelberg D E, Parnes H, McLeod D G, Harold N, Peer C, Yu Y, Tomita Y, Lee M J, Lee S, Trepel J B, Gulley J L, Figg W D, Dahut W L. A phase I study of TRC105 anti-endoglin (CD105) antibody in metastatic castration-resistant prostate cancer. BJU international. 2015; 116(4):546-55).

Based on these analyses, Om-ASCo is incubated in the pre-adipocyte media supplemented with a cocktail containing bFGF and TRC105 separately or in combination. TRC105 is added at about 5-50 pM dose range (it has high avidity for endoglin) while bFGF is added at about 100-500 nM dose ranges. A time curve 1-8 days for incubation is optimized. The treated om-ASCo is analyzed as described below.

Separately, lncRNAs MALAT1 or GAS5 or linc-VLDLR is over-expressed (Plasmids from Addgene, 1-3 µg/35 mm plate; transfection for 24-72 hours) in om-ASCo. Transfections are performed using Nucleofector, Amaxa, program A-033. Cells are maintained in pre-adipocyte media for 48 hours and harvested for analysis as below. Transfection efficiency in ASC is optimized in the inventor's lab (Patel R S, Carter G, Bassit G E, Patel A A, Cooper D R, Murr M, Patel N A. Adipose-derived stem cells from lean and obese humans show depot specific differences in their stem cell markers, exosome contents and senescence: Role of Protein Kinase C delta (PKCδ) in adipose stem cell niche. Stem Cell Investigations. 2016, 3(1); Carter G, Apostolatos A, Patel R. Mathur A, Cooper D, Murr M, Patel N A. Dysregulated Alternative Splicing Pattern of PKC during Differentiation of Human Preadipocytes Represents Distinct Differences between Lean and Obese Adipocytes. ISRN Obesity. 2013, 2013:9; Carter G, Patel R S, Apostolatos A, Murr M, Cooper D R, Patel N A. Protein kinase C delta splice variant modulates senescence via hTERT in adipose derived stem cells. Stem Cell Investigations. 2014, 1(3). Epub January 2014).

The goal is to bring om-ASCo to sc-ASCn stem cell transcription factor expression levels. The cells are sorted by FACS and seeded into fresh plates—this hybrid ASC is referred to as Scutal from here on.

Complete characterization of the Scutal ASCs is used in FACs for the stem cell markers and antigens: CD31, CD34, CD44, CD45, CD73, CD90, CD105, CD106, and CD117. Real time qPCR is performed for transcription factors such as Nanog, Sox2, Sox15, Oct4, Sal4, KLF4 and BMI1; LncRNAs: MALAT1, GAS5, linc-VLDLR as well as lncRNA array for 84 lncRNAs. Additional noncoding RNA profiles and gene expression arrays are studied as described above.

Scutal is differentiated in vitro to mature adipocytes (Patel R S, Carter G, Bassit G E, Patel A A, Cooper D R. Murr M, Patel N A. Adipose-derived stem cells from lean and obese humans show depot specific differences in their stem cell markers, exosome contents and senescence: Role of Protein Kinase C delta (PKCδ) in adipose stem cell niche. Stem Cell Investigations. 2016, 3(1); Carter G, Apostolatos A, Patel R, Mathur A, Cooper D, Murr M, Patel N A. Dysregulated Alternative Splicing Pattern of PKC during Differentiation of Human Preadipocytes Represents Distinct Differences between Lean and Obese Adipocytes. ISRN Obesity. 2013, 2013:9; J E W, Patel N A, Carter G, Moor A, Patel R, Ghansah T, Mathur A, Murr M, Bickford P, Gould L, Cooper D R. Comparison of markers and functional attributes of human adipose derived stem cells and dedifferentiated adipocyte cells from subcutaneous fat of an obese diabetic donor. Advances in Wound Care. 2013; WOUND-2013-0452.R1 (September 2013); Carter G, Patel R S, Apostolatos A, Murr M, Cooper D R, Patel N A. Protein kinase C delta splice variant modulates senescence via hTERT in adipose derived stem cells. Stem Cell Investigations. 2014; 1(3)). Secretion of free fatty acids and cytokines is analyzed. The leptin:adiponectin ratio (hormones secreted by adipocytes that modulate appetite, innate immune function; sensitive marker for metabolic syndrome) is determined in the secretome as well as within adipocytes. The secretome of scutal is analyzed by human MAP (Myriad) and transcriptomics as the omental depot secretes into the portal circulation which impacts other organs.

Since omental depots have increased levels of apoptosis and inflammation which is correlated to metabolic syndrome, diabetes and other morbidities, apoptosis gene profiles are generated on ASC and adipocytes for Bcl2, Bcl-xS/L, caspase9a/b, caspase3 using real time qPCR and western blot analysis and Annexin V/PI for apoptosis. The pro- and anti-inflammatory markers: TNFα, IL-13, IL-6, IL-8, IL-10, and MCP1 are determined using real time qPCR and western blot analysis. Flow cytometry is used for M1 macrophages (CD11c +ve) and M2 macrophages (CD206 +ve) to analyze adipocyte infiltration by macrophages. The benchmark for mature Scutal adipocytes is higher levels and secretion of leptin and lower inflammatory cytokines; reduced adipocyte stress by modulation of adipogenesis; and lipogenesis.

Additionally, the inventors evaluate if manipulation of amounts of lncRNA or transcription factors in ASC affected the adipocyte size or lipid content of mature adipocytes using DAPI/Nile staining, Spectre adipocyte size analysis (Millipore) and Oil Red O staining for lipids. These methods are optimized by the lab (Patel R S, Carter G, Bassit G E, Patel A A, Cooper D R, Murr M, Patel N A. Adipose-derived stem cells from lean and obese humans show depot specific differences in their stem cell markers, exosome contents and senescence: Role of Protein Kinase C delta (PKCδ) in adipose stem cell niche. Stem Cell Investigations. 2016, 3(1); Carter G, Apostolatos A, Patel R, Mathur A, Cooper D, Murr M, Patel N A. Dysregulated Alternative Splicing Pattern of PKC during Differentiation of Human Preadipocytes Represents Distinct Differences between Lean and Obese Adipocytes. ISRN Obesity. 2013, 2013:9, J E W, Patel N A, Carter G, Moor A, Patel R, Ghansah T, Mathur A, Murr M, Bickford P, Gould L, Cooper D R. Comparison of markers and functional attributes of human adipose derived stem cells and dedifferentiated adipocyte cells from subcutaneous fat of an obese diabetic donor. Advances in Wound Care. 2013, WOUND-2013-0452; Carter G, Patel R S, Apostolatos A, Murr M, Cooper D R, Patel N A. Protein kinase C delta splice variant modulates senescence via hTERT in adipose derived stem cells. Stem Cell Investigations. 2014; 1(3)).

Metabolomics

The inventors generate the complete metabolite and biochemical status of Scutal adipocytes such that the changes in the networks and pathways are deciphered which provide insights into physiological and pathological states.

Conclusion

This innovative approach of reprogramming om-ASCo to a subcutaneous-like lineage has tremendous therapeutic potential as it will render the omental obese depot metabolically healthy/protected. The hybrid Scutal ASC and adipocytes are systematically characterized.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of altering a metabolic profile of omental obese adipose cells to a subcutaneous lean adipose cells metabolic profile comprising exposing the omental obese adipose cells in vitro to conditioned medium from cultures of subcutaneous lean adipose derived stem cell.

2. The method of claim 1, wherein expression of transcription factors of the omental obese adipose stem cells is changed.

3. The method of claim 2, wherein the expression of transcription factors of the omental obese adipose cells resembles a subcutaneous lean adipose stem cell transcription profile.

4. The method of claim 1, wherein the omental obese adipose stem cells are exposed to 50% v/v of the conditioned medium.

5. The method of claim 1, wherein the omental obese adipose cells are exposed to the conditioned medium for 72 hours.

6. The method of claim 1, wherein the conditioned medium contains elevated expression of long noncoding RNAs (lncRNAs) MALAT1, GAS5, and linc-VLDLR.

7. The method of claim 1, wherein the conditioned medium contains elevated levels of basic fibroblast growth factor (bFGF).

8. The method of claim 1, wherein transcription factors Sox15 and Oct4 are upregulated in the omental obese adipose cells after exposure to the conditioned medium.

9. A method of altering omental obese adipose cells metabolic profile to a subcutaneous lean adipose cells metabolic profile comprising exposing the omental obese adipose cells in vitro to exosomes from conditioned media of subcutaneous lean adipose derived stem cells.

10. The method of claim 9, wherein expression of transcription factors of the omental obese adipose stem cells is changed.

11. The method of claim 10, wherein the expression of transcription factors of the omental adipose obese cells resembles a subcutaneous lean adipose stem cell transcription profile.

12. The method of claim 9, wherein the omental obese adipose stem cells are exposed to 10 μg exosomes.

13. The method of claim 9, wherein the omental adipose obese cells are exposed to the exosomes for 72 hours.

14. The method of claim 9, wherein the transcription factors Sox 15 and Oct4 are upregulated in the omental adipose cells exposed to the exosomes.

15. The method of claim 9, wherein the exosomes contain elevated expression of long noncoding RNAs (lncRNAs) MALAT1, GAS5, and linc-VLDLR.

16. The method of claim 9, wherein the exosomes contain elevated levels of basic fibroblast growth factor (bFGF).

* * * * *

UNITED STATES PATENT AND TRADEMARK OFFICE
CERTIFICATE OF CORRECTION

PATENT NO.        : 10,196,612 B1
APPLICATION NO.   : 15/646902
DATED             : February 5, 2019
INVENTOR(S)       : Niketa A. Patel and Ghattas El Bassit Page 1 of 1

It is certified that error appears in the above-identified patent and that said Letters Patent is hereby corrected as shown below:

On the Title Page

Item (73) Assignees should read:
FL (US); United States Government as Represented by the Department of Veterans Affairs, Signed and Sealed this
Nineteenth Day of March, 2019

Andrei Iancu
*Director of the United States Patent and Trademark Office*